United States Patent
Dittrich et al.

(10) Patent No.: US 12,390,259 B2
(45) Date of Patent: Aug. 19, 2025

(54) LINEAR ELECTRIC SURGICAL HAMMER IMPACT TOOL

(71) Applicant: Zimmer, Inc., Warsaw, IN (US)

(72) Inventors: Joshua Dittrich, Warsaw, IN (US); Neil Singer, Warsaw, IN (US); Ken Pasch, Warsaw, IN (US); Alexander Slocum, Bow, NH (US); Nitin Goyal, Mclean, VA (US)

(73) Assignee: Zimmer, Inc., Warsaw, IN (US)

( * ) Notice: Subject to any disclaimer, the term of this patent is extended or adjusted under 35 U.S.C. 154(b) by 218 days.

(21) Appl. No.: 18/222,830

(22) Filed: Jul. 17, 2023

(65) Prior Publication Data
US 2024/0024012 A1    Jan. 25, 2024

Related U.S. Application Data

(60) Provisional application No. 63/450,316, filed on Mar. 6, 2023, provisional application No. 63/390,354, filed on Jul. 19, 2022.

(51) Int. Cl.
*A61B 17/92*   (2006.01)

(52) U.S. Cl.
CPC ........ *A61B 17/92* (2013.01); *A61B 2017/924* (2013.01); *A61B 2017/928* (2013.01)

(58) Field of Classification Search
CPC .......................... A61B 17/92; A61B 2017/924
See application file for complete search history.

(56) References Cited

U.S. PATENT DOCUMENTS

| | | | |
|---|---|---|---|
| 2,542,695 A | * | 2/1951 | Neff ........................ A61B 17/92 D24/142 |
| 2,576,851 A | | 11/1951 | Newman |
| 2,655,921 A | | 10/1953 | Haboush |
| 3,450,215 A | | 6/1969 | Emery |

(Continued)

FOREIGN PATENT DOCUMENTS

| | | |
|---|---|---|
| AU | 2019203142 A1 | 11/2019 |
| AU | 2020200771 A1 | 2/2020 |

(Continued)

OTHER PUBLICATIONS

"U.S. Appl. No. 17/587,794, Response filed Aug. 28, 2023 to Restriction Requirement mailed Jun. 27, 2023", 7 pgs.

(Continued)

*Primary Examiner* — Christian A Sevilla
(74) *Attorney, Agent, or Firm* — SCHWEGMAN LUNDBERG & WOESSNER, P.A.

(57) ABSTRACT

Disclosed herein are linear electric surgical hammer impact tools and methods of use thereof. The linear electric surgical hammer impact tools can include a shuttle located inside a cavity of a housing. A wall of the shuttle defines a plurality of grooves extend from a first end of the shuttle to a second end of the shuttle. A piston can be located at least partially within the shuttle and arranged along the longitudinal axis of the housing. The piston includes protrusions and each of the protrusions can be arranged to travel within a respective one of the grooves of the shuttle. Motion of the piston in a first direction causes the piston to contact the first end of the shuttle and motion of the piston in a second direction causes the piston to contact the second end of the shuttle.

21 Claims, 14 Drawing Sheets

(56) References Cited

U.S. PATENT DOCUMENTS

| | | | |
|---|---|---|---|
| 3,472,323 A | | 10/1969 | Hall |
| 3,626,935 A | | 12/1971 | Pollock et al. |
| 3,752,161 A | | 8/1973 | Bent |
| 3,829,974 A | * | 8/1974 | McShirley ............ A61C 3/08 |
| | | | 433/124 |
| 4,298,074 A | * | 11/1981 | Mattchen .......... A61B 17/1624 |
| | | | 606/104 |
| 4,466,429 A | | 8/1984 | Loscher et al. |
| 4,651,833 A | | 3/1987 | Karpf et al. |
| 4,834,092 A | | 5/1989 | Alexson et al. |
| 5,057,112 A | | 10/1991 | Sherman et al. |
| 5,108,400 A | | 4/1992 | Appel et al. |
| 5,152,352 A | | 10/1992 | Mandanis |
| 5,163,519 A | | 11/1992 | Mead et al. |
| 5,210,918 A | | 5/1993 | Wozniak et al. |
| 5,282,805 A | | 2/1994 | Richelsoph et al. |
| 5,352,230 A | | 10/1994 | Hood |
| 5,353,230 A | | 10/1994 | Maejima et al. |
| 5,363,726 A | | 11/1994 | Smith |
| 5,431,660 A | | 7/1995 | Burke |
| 5,485,887 A | | 1/1996 | Mandanis |
| 5,553,675 A | | 9/1996 | Pitzen et al. |
| 5,868,756 A | * | 2/1999 | Henry ..................... G10K 9/10 |
| | | | 606/128 |
| 6,126,694 A | | 10/2000 | Gray, Jr. |
| 6,159,214 A | | 12/2000 | Michelson |
| 6,264,660 B1 | | 7/2001 | Schmidt et al. |
| 6,264,661 B1 | | 7/2001 | Jerger et al. |
| 6,368,324 B1 | | 4/2002 | Dinger |
| 6,520,266 B2 | | 2/2003 | Bongers-ambrosius et al. |
| 6,626,913 B1 | | 9/2003 | Mckinnon et al. |
| 6,814,738 B2 | | 11/2004 | Naughton et al. |
| 6,868,918 B2 | | 3/2005 | Shinohara |
| 7,090,677 B2 | | 8/2006 | Fallin et al. |
| 7,189,241 B2 | | 3/2007 | Yoon et al. |
| 7,637,327 B2 | | 12/2009 | Gruenig |
| 7,874,839 B2 | * | 1/2011 | Bouneff ................ A61C 1/148 |
| | | | 433/121 |
| 8,002,776 B2 | | 8/2011 | Liu et al. |
| 8,393,409 B2 | | 3/2013 | Pedicini |
| 8,444,647 B2 | | 5/2013 | Walen et al. |
| 8,465,492 B2 | | 6/2013 | Estes |
| 8,556,901 B2 | | 10/2013 | Anthony et al. |
| 8,602,124 B2 | | 12/2013 | Pedicini |
| 8,695,726 B2 | | 4/2014 | Pedicini |
| 8,894,654 B2 | | 11/2014 | Anderson |
| 8,936,105 B2 | | 1/2015 | Pedicini |
| 8,936,106 B2 | | 1/2015 | Pedicini |
| 9,168,154 B2 | | 10/2015 | Behzadi |
| 9,186,158 B2 | | 11/2015 | Anthony et al. |
| 9,198,675 B2 | | 12/2015 | Nelson et al. |
| 9,220,612 B2 | | 12/2015 | Behzadi |
| 9,554,965 B2 | | 1/2017 | Foehrenbach |
| 9,629,641 B2 | | 4/2017 | Ferro et al. |
| 9,649,202 B2 | | 5/2017 | Behzadi et al. |
| 9,877,734 B2 | | 1/2018 | Anderson |
| 9,901,354 B2 | | 2/2018 | Pedicini |
| 9,931,151 B2 | | 4/2018 | Donald et al. |
| 9,943,318 B2 | | 4/2018 | Anthony et al. |
| RE46,954 E | | 7/2018 | Pedicini |
| 10,028,754 B2 | | 7/2018 | Johnson et al. |
| RE46,979 E | | 8/2018 | Pedicini |
| 10,159,500 B2 | | 12/2018 | Chavarria et al. |
| 10,172,722 B2 | | 1/2019 | Behzadi et al. |
| 10,245,160 B2 | | 4/2019 | Behzadi |
| 10,245,162 B2 | | 4/2019 | Behzadi et al. |
| 10,251,663 B2 | | 4/2019 | Behzadi |
| 10,299,930 B2 | | 5/2019 | Behzadi |
| 10,342,591 B2 | | 7/2019 | Pedicini |
| 10,368,882 B2 | | 8/2019 | Ferro et al. |
| 10,413,425 B2 | | 9/2019 | Behzadi et al. |
| 10,426,540 B2 | | 10/2019 | Behzadi |
| 10,441,244 B2 | | 10/2019 | Behzadi |
| 10,456,271 B2 | | 10/2019 | Behzadi |
| 10,463,505 B2 | | 11/2019 | Behzadi |
| 10,470,897 B2 | | 11/2019 | Behzadi |
| 10,478,318 B2 | | 11/2019 | Behzadi et al. |
| 10,568,643 B2 | | 2/2020 | Johnson et al. |
| 10,603,173 B2 | | 3/2020 | Carr et al. |
| RE47,963 E | | 4/2020 | Pedicini |
| 10,610,379 B2 | | 4/2020 | Behzadi |
| RE47,997 E | | 5/2020 | Pedicini |
| 10,653,533 B2 | | 5/2020 | Behzadi et al. |
| 10,660,767 B2 | | 5/2020 | Behzadi |
| 10,729,559 B2 | | 8/2020 | Behzadi et al. |
| RE48,184 E | | 9/2020 | Pedicini |
| RE48,251 E | | 10/2020 | Pedicini |
| 11,013,503 B2 | | 5/2021 | Pedicini |
| 11,490,943 B2 | | 11/2022 | Haiat et al. |
| 11,918,268 B2 | | 3/2024 | Doyle |
| 11,925,359 B2 | | 3/2024 | Slocum et al. |
| 12,004,793 B2 | | 6/2024 | Levy |
| 2004/0026097 A1 | | 2/2004 | Hecht |
| 2007/0282345 A1 | | 12/2007 | Yedlicka et al. |
| 2010/0137760 A1 | | 6/2010 | Schulz et al. |
| 2011/0255927 A1 | | 10/2011 | Boudreau et al. |
| 2011/0270256 A1 | | 11/2011 | Nelson et al. |
| 2012/0172939 A1 | | 7/2012 | Pedicini |
| 2012/0215267 A1 | | 8/2012 | Pedicini |
| 2012/0259339 A1 | | 10/2012 | Hood et al. |
| 2013/0161050 A1 | | 6/2013 | Pedicini |
| 2013/0261681 A1 | | 10/2013 | Bittenson |
| 2014/0318819 A1 | | 10/2014 | Pedicini |
| 2014/0318823 A1 | | 10/2014 | Pedicini |
| 2015/0196343 A1 | | 7/2015 | Donald et al. |
| 2016/0199199 A1 | | 7/2016 | Pedicini |
| 2017/0020536 A1 | | 1/2017 | Johnson et al. |
| 2017/0056205 A1 | | 3/2017 | Biegun et al. |
| 2018/0055518 A1 | | 3/2018 | Pedicini |
| 2018/0055552 A1 | | 3/2018 | Pedicini |
| 2018/0303496 A1 | | 10/2018 | Johnson et al. |
| 2018/0318089 A1 | | 11/2018 | Carr et al. |
| 2018/0360464 A1 | | 12/2018 | Irvine |
| 2019/0167434 A1 | | 6/2019 | Satterthwaite et al. |
| 2019/0183554 A1 | | 6/2019 | Pedicini |
| 2019/0216521 A1 | | 7/2019 | Chhatrala |
| 2019/0247057 A1 | | 8/2019 | Anderson |
| 2019/0282286 A1 | | 9/2019 | Pedicini |
| 2022/0142693 A1 | | 5/2022 | Slocum et al. |
| 2022/0226033 A1 | | 7/2022 | Slocum et al. |
| 2022/0240946 A1 | | 8/2022 | Slocum et al. |
| 2022/0240947 A1 | | 8/2022 | Marinkovich |
| 2022/0240998 A1 | | 8/2022 | Slocum |
| 2022/0273317 A1 | | 9/2022 | Levy |
| 2022/0361934 A1 | | 11/2022 | Pedicini |
| 2023/0240735 A1 | | 8/2023 | Doyle |

FOREIGN PATENT DOCUMENTS

| | | |
|---|---|---|
| AU | 2021239844 A1 | 10/2022 |
| AU | 2017320580 B2 | 4/2023 |
| AU | 2021378282 A1 | 6/2023 |
| AU | 2022227599 A1 | 8/2023 |
| CA | 3063569 A1 | 11/2018 |
| CA | 3209081 A1 | 8/2022 |
| CA | 3211071 A1 | 9/2022 |
| CH | 701397 A2 | 1/2011 |
| CN | 2423872 Y | 3/2001 |
| CN | 204863450 U | 12/2015 |
| CN | 109070324 A | 12/2018 |
| CN | 108602180 B | 12/2022 |
| CN | 116801840 A | 9/2023 |
| CN | 117414174 A | 1/2024 |
| DE | 102010017726 A1 | 1/2011 |
| EP | 0290375 A1 | 11/1988 |
| FR | 2054809 A5 | 5/1971 |
| JP | H06229427 A | 8/1994 |
| JP | H10174689 A | 6/1998 |
| JP | 2002144255 A | 5/2002 |
| JP | 2005506211 A | 3/2005 |
| JP | 2010524577 A | 7/2010 |
| JP | 2013036488 A | 2/2013 |
| JP | 2015517341 A | 6/2015 |
| JP | 2016202560 A | 12/2016 |

(56) References Cited

FOREIGN PATENT DOCUMENTS

| | | |
|---|---|---|
| JP | 2018502689 A | 2/2018 |
| JP | 2019524165 A | 9/2019 |
| JP | 2019177138 A | 10/2019 |
| JP | 2019198645 A | 11/2019 |
| JP | 2020530332 A | 10/2020 |
| JP | 2020185421 A | 11/2020 |
| JP | 7127068 B2 | 8/2022 |
| JP | 2022166207 A | 11/2022 |
| JP | 7366968 B2 | 10/2023 |
| JP | 7375104 B2 | 10/2023 |
| JP | 7404463 B2 | 12/2023 |
| JP | 2023551117 A | 12/2023 |
| JP | 2024013234 A | 1/2024 |
| JP | 2024504977 A | 2/2024 |
| JP | 2024505231 A | 2/2024 |
| JP | 2024505239 A | 2/2024 |
| JP | 2024505543 A | 2/2024 |
| JP | 2024507954 A | 2/2024 |
| WO | WO-8802246 A2 | 4/1988 |
| WO | WO-8906516 A1 | 7/1989 |
| WO | WO-2008130904 A2 | 10/2008 |
| WO | WO-2016112397 A1 | 7/2016 |
| WO | WO-2018044348 A1 | 3/2018 |
| WO | WO-2018217250 A1 | 11/2018 |
| WO | WO-2022103835 A1 | 5/2022 |
| WO | WO-2022159704 A1 | 7/2022 |
| WO | WO-2022165215 A1 | 8/2022 |
| WO | WO-2022165223 A1 | 8/2022 |
| WO | WO-2022165357 A1 | 8/2022 |
| WO | WO-2022182772 A1 | 9/2022 |

OTHER PUBLICATIONS

"International Application Serial No. PCT/US2022/013312, International Preliminary Report on Patentability mailed Aug. 3, 2023", 12 pgs.
"International Application Serial No. PCT/US2022/014368, International Preliminary Report on Patentability mailed Aug. 10, 2023", 10 pgs.
"International Application Serial No. PCT/US2022/014380, International Preliminary Report on Patentability mailed Aug. 10, 2023", 9 pgs.
"International Application Serial No. PCT/US2022/014596, International Preliminary Report on Patentability mailed Aug. 10, 2023", 7 pgs.
"International Application Serial No. PCT/US2022/017537, International Preliminary Report on Patentability mailed Sep. 7, 2023", 7 pgs.
"U.S. Appl. No. 17/587,794, Notice of Allowance mailed Nov. 15, 2023", 10 pgs.
"U.S. Appl. No. 17/587,866, Notice of Allowance mailed Apr. 11, 2024", 17 pgs.
"U.S. Appl. No. 17/678,807, Notice of Allowance mailed Feb. 14, 2024", 16 pgs.
"Australian Application Serial No. 2021378282, First Examination Report mailed Mar. 7, 2024", 3 pgs.
"European Application Serial No. 21820393.3, Response Filed Dec. 14, 2023 to Communication pursuant to Rules 161(1) and 162 EPC mailed Jul. 6, 2023", 10 pgs.
"European Application Serial No. 23186404.2, Extended European Search Report mailed Nov. 23, 2023", 8 pgs.
"U.S. Appl. No. 17/523,540, Notice of Allowance mailed Apr. 22, 2024", 10 pgs.
"Australian Application Serial No. 2021378282, Response filed May 22, 2024 to First Examination Report mailed Mar. 7, 2024", 8 pgs.
"Australian Application Serial No. 2022211325, First Examination Report mailed Apr. 29, 2024", 3 pgs.
"Australian Application Serial No. 2022211325, Response filed Jul. 19, 2024 to First Examination Report mailed Apr. 29, 2024", 17 pgs.
"Australian Application Serial No. 2022212126, First Examination Report mailed Apr. 26, 2024", 3 pgs.
"Australian Application Serial No. 2022212126, Response Filed Jul. 2, 2024 to First Examination Report mailed Apr. 26, 2024", 16 pgs.
"Australian Application Serial No. 2022212275, First Examination Report mailed May 15, 2024", 2 pgs.
"Australian Application Serial No. 2022212275, Response Filed Jun. 19, 2024 to First Examination Report mailed May 15, 2024", 14 pgs.
"Australian Application Serial No. 2022214931, First Examination Report mailed May 7, 2024", 3 pgs.
"Australian Application Serial No. 2022214931, Response filed Jul. 26, 2024 to First Examination Report mailed May 7, 2024", 9 pgs.
"Australian Application Serial No. 2022227599, First Examination Report mailed Apr. 18, 2024", 2 pgs.
"Australian Application Serial No. 2022227599, Response Filed Sep. 27, 2024 to First Examination Report mailed Apr. 18, 2024", 14 pgs.
"Australian Application Serial No. 2023206091, First Examination Report mailed Apr. 19, 2024", 4 pgs.
"Australian Application Serial No. 2023206091, Response filed Jul. 5, 2024 to First Examination Report mailed Apr. 19, 2024", 13 pgs.
"European Application Serial No. 22703776.9, Response Filed Mar. 11, 2024 to Communication pursuant to Rules 161(1) and 162 EPC mailed Aug. 30, 2023", 9 pgs.
"European Application Serial No. 22704684.4, Response filed Mar. 18, 2024 to Communication pursuant to Rules 161(1) and 162 EPC mailed Sep. 7, 2023", 17 pgs.
"European Application Serial No. 22705238.8, Response Filed Mar. 18, 2024 to Communication pursuant to Rules 161(1) and 162 EPC mailed Sep. 8, 2023", 172 pgs.
"European Application Serial No. 22705250.3, Response Filed Mar. 18, 2024 to Communication pursuant to Rules 161(1) and 162 EPC mailed Sep. 8, 2023", 15 pgs.
"European Application Serial No. 22713111.7, Response Filed Apr. 15, 2024 to Communication pursuant to Rules 161(1) and 162 EPC mailed Oct. 4, 2024", 8 pgs.
"European Application Serial No. 24161610.1, Extended European Search Report mailed Jul. 10, 2024", 6 pgs.
"Japanese Application Serial No. 2023-117628, Notification of Reasons for Refusal mailed May 28, 2024", w/ English translation, 7 pgs.
"Japanese Application Serial No. 2023-527766, Notification of Reasons for Refusal mailed Apr. 16, 2024", w/ English translation, 6 pgs.
"Japanese Application Serial No. 2023-544157, Notice of Reasons for Rejection mailed Apr. 23, 2024", w/ English translation, 5 pgs.
"Japanese Application Serial No. 2023-546065, Notification of Reasons for Refusal mailed Apr. 16, 2024", w/ English Translation, 15 pgs.
"Japanese Application Serial No. 2023-546135, Notification of Reasons for Refusal mailed Apr. 16, 2024", w/ English Translation, 9 pgs.
"Japanese Application Serial No. 2023-546333, Notification of Reasons for Refusal mailed Apr. 16, 2024", w/ English translation, 8 pgs.
"Japanese Application Serial No. 2023-552050, Notification of Reasons for Rejection mailed Jul. 2, 2024", W/English Translation, 5 pgs.
U.S. Appl. No. 17/523,540, filed Nov. 10, 2021, Bi-Spring Surgical Impact Tool.
U.S. Appl. No. 17/581,316, filed Jan. 21, 2022, Linear Electric Surgical Hammer Impact Tool.
U.S. Appl. No. 17/587,794, filed Jan. 28, 2022, Rotary Electric Surgical Hammer Impact Tool.
U.S. Appl. No. 17/587,866, filed Jan. 28, 2022, Orthopedic Impactor Tool.
U.S. Appl. No. 17/678,807, filed Feb. 23, 2022, Bi-Spring Surgical Hammer Impact Tools.
U.S. Appl. No. 17/589,456, filed Jan. 31, 2022, Tri-Roll Thread Electric Surgical Impacct Tool.
"U.S. Appl. No. 17/587,794, Restriction Requirement mailed Jun. 27, 2023", 7 pgs.

(56) References Cited

OTHER PUBLICATIONS

"International Application Serial No. PCT/US2021/058776, International Preliminary Report on Patentability mailed May 25, 2023", 10 pgs.

"International Application Serial No. PCT/US2021/058776, International Search Report mailed Feb. 9, 2022", 5 pgs.

"International Application Serial No. PCT/US2021/058776, Written Opinion mailed Feb. 9, 2022", 8 pgs.

"International Application Serial No. PCT/US2022/013312, International Search Report mailed Jun. 24, 2022", 6 pgs.

"International Application Serial No. PCT/US2022/013312, Invitation to Pay Additional Fees mailed May 3, 2022", 5 pgs.

"International Application Serial No. PCT/US2022/013312, Written Opinion mailed Jun. 24, 2022", 10 pgs.

"International Application Serial No. PCT/US2022/014368, International Search Report mailed May 30, 2022", 7 pgs.

"International Application Serial No. PCT/US2022/014368, Invitation to Pay Additional Fees mailed Apr. 5, 2022", 10 pgs.

"International Application Serial No. PCT/US2022/014368, Written Opinion mailed May 30, 2022", 8 pgs.

"International Application Serial No. PCT/US2022/014380, International Search Report mailed Jun. 24, 2022", 6 pgs.

"International Application Serial No. PCT/US2022/014380, Invitation to Pay Additional Fees mailed May 3, 2022", 5 pgs.

"International Application Serial No. PCT/US2022/014380, Written Opinion mailed Jun. 24, 2022", 7 pgs.

"International Application Serial No. PCT/US2022/014596, International Search Report mailed May 10, 2022", 4 pgs.

"International Application Serial No. PCT/US2022/014596, Written Opinion mailed May 10, 2022", 5 pgs.

"International Application Serial No. PCT/US2022/017537, International Search Report mailed Jun. 1, 2022", 4 pgs.

"International Application Serial No. PCT/US2022/017537, Written Opinion mailed Jun. 1, 2022", 5 pgs.

Budimir, Miles, "What is a rack and roller pinion?", [Online]. Retrieved from the Internet: <https://www.motioncontroltips.com/rack-roller-pinion/>, (Nov. 10, 2017), 13 pgs.

Nexen, "Rack and Roller Pinion System", [Online]. Retrieved from the Internet: <https://www.nexengroup.com/nxn/products/prod-nav/lp/Roller+Pinion+System>, (Accessed online Apr. 27, 2021), 10 pgs.

* cited by examiner

LINEAR ELECTRIC SURGICAL HAMMER IMPACT TOOL

CROSS-REFERENCE TO RELATED APPLICATIONS

This application claims the benefit of U.S. Provisional Patent Application Ser. No. 63/390,354, filed on Jul. 19, 2022, and also claims the benefit of U.S. Provisional Patent Application Ser. No. 63/450,316, filed on Mar. 6, 2023, the benefit of priority of each of which is claimed hereby, and each of which is incorporated by reference herein in its entirety.

The present application is related to U.S. Provisional Application No. 63/140,071, entitled "Linear Electric Hammer Impact Tool," filed on Jan. 21, 2021, and U.S. Non-Provisional application Ser. No. 17/581,316, entitled Linear Electric Surgical Hammer Impact Tool," filed on Jan. 21, 2022; the contents of which are hereby incorporated by reference in their entirety.

FIELD OF THE DISCLOSURE

The present disclosure relates generally to surgical instruments and use thereof. More specifically, the present disclosure relates to an electric surgical impact tool and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stem of a hip implant. Such broaches can be used with a hammer wielded by the physician or with a pneumatic "jackhammer" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is a linear electric surgical hammer impact tool comprising: a housing defining a cavity extending along a longitudinal axis of the housing; a shuttle located inside the cavity and arranged along the longitudinal axis of the housing, the shuttle comprising a first end, a second end, and a wall extending from the first end to the second end, the wall defining a plurality of grooves extend from a first end of the shuttle to a second end of the shuttle; a piston located at least partially within the shuttle and arranged along the longitudinal axis of the housing, the piston comprising a plurality of protrusions, each of the plurality of protrusion arranged to travel within a respective one of the plurality of grooves of the shuttle; a motor configured to drive the piston along the longitudinal axis in a first direction and a second direction; and a tool holder connected to the shuttle, wherein motion of the piston in a first direction causes the piston to contact the first end of the shuttle and motion of the piston in a second direction causes the piston to contact the second end of the shuttle.

In Example 2, the subject matter of Example 1 optionally includes a cap connected to a proximal end of the housing; and a first biasing member located in between the first end of the shuttle and the cap.

In Example 3, the subject matter of any one or more of Examples 1-2 optionally include a partition located within the housing; and a second biasing member located in between the second end of the shuttle and the partition.

In Example 4, the subject matter of any one or more of Examples 2-3 optionally include wherein at least one of the first biasing member and the second biasing member comprise a spring.

In Example 5, the subject matter of any one or more of Examples 1-4 optionally include wherein each of the plurality of protrusions comprises a polymer.

In Example 6, the subject matter of Example 5 optionally includes wherein the polymer is impregnated with a lubricant.

In Example 7, the subject matter of any one or more of Examples 1-6 optionally include wherein the plurality of protrusions are straight.

In Example 8, the subject matter of any one or more of Examples 1-7 optionally include a sensor arrange to detect a position of the shuttle within the cavity.

In Example 9, the subject matter of any one or more of Examples 1-8 optionally include wherein the tool holder comprises a quick connect/disconnect chuck.

In Example 10, the subject matter of any one or more of Examples 1-9 optionally include a handle that defines a cavity sized to receive electronics and a trigger.

In Example 11, the subject matter of any one or more of Examples 1-10 optionally include wherein the tool holder threadably connects to the shuttle.

In Example 12, the subject matter of any one or more of Examples 1-11 optionally include wherein a distal surface of the tool holder forms an impact surface.

Example 13 is a linear electric surgical hammer impact tool comprising: a housing defining a cavity extending along a longitudinal axis of the housing; a shuttle located inside the cavity and arranged along the longitudinal axis of the housing, the shuttle comprising a first end, a second end, and a wall extending from the first end to the second end, the wall defining a plurality of grooves extend from a first end of the shuttle to a second end of the shuttle; a piston located at least partially within the shuttle and arranged along the longitudinal axis of the housing, the piston comprising a plurality of protrusions and a flange, each of the plurality of protrusion arranged to travel within a respective one of the plurality of grooves of the shuttle; a motor configured to drive the piston along the longitudinal axis in a first direction and a second direction; and a tool holder threadably connected to the shuttle, the tool holder comprising a distal surface that forms an impact surface, wherein motion of the piston in a first direction causes the piston to contact the impact surface of the tool holder and motion of the piston in a second direction causes the flange of the piston to contact the second end of the shuttle.

In Example 14, the subject matter of Example 13 optionally includes a cap connected to a proximal end of the housing; and a first biasing member located in between the first end of the shuttle and the cap.

In Example 15, the subject matter of any one or more of Examples 13-14 optionally include a partition located within the housing; and a second biasing member located in between the second end of the shuttle and the partition.

In Example 16, the subject matter of any one or more of Examples 13-15 optionally include wherein at least one of the first biasing member and the second biasing member comprise a spring.

In Example 17, the subject matter of any one or more of Examples 13-16 optionally include wherein each of the plurality of protrusions comprises a polymer impregnated with a lubricant.

In Example 18, the subject matter of any one or more of Examples 13-17 optionally include wherein the plurality of protrusions are straight.

In Example 19, the subject matter of any one or more of Examples 13-18 optionally include a sensor arrange to detect a position of the shuttle within the cavity.

In Example 20, the subject matter of any one or more of Examples 13-19 optionally include wherein the tool holder comprises a quick connect/disconnect chuck.

In Example 21, the subject matter of any one or more of Examples 13-20 optionally include a handle that defines a cavity sized to receive electronics and a trigger.

In Example 21, the surgical impact tools, systems, and/or methods of any one or any combination of Examples 1-20 can optionally be configured such that all elements or options recited are available to use or select from.

Example 22 is a linear electric surgical hammer impact tool comprising: a housing defining a cavity extending along a longitudinal axis of the housing; a shuttle located inside the cavity and arranged along the longitudinal axis of the housing, the shuttle comprising a first end, a second end, and a wall extending from the first end to the second end, the wall including opposing exterior key grooves extending a length of an exterior portion of the wall; a hammer assembly located at least partially within a proximal end of the shuttle and arranged along the longitudinal axis of the housing; a linear electric motor configured to drive the piston along the longitudinal axis in a first direction and a second direction; and an impact assembly located at least partially within a distal end of the shuttle. The linear electric impact tool operates by motion of the hammer assembly in a first direction causing the hammer assembly to contact the first end of the shuttle to generate a forward impact and motion of the hammer assembly in a second direction causing the hammer assembly to contact the second end of the shuttle to generate a reverse impact.

In Example 23, the subject matter of Example 22 can optionally include the hammer assembly having an impact piston surrounding an impact hammer.

In Example 24, the subject matter of any one of Examples 22 or 23 can optionally include the impact hammer having a curved proximal contact surface.

In Example 25, the subject matter of any one of Examples 22 to 24 can optionally include the curved proximal contact surface having a radius of 100 mm.

In Example 26, the subject matter of any one of Examples 22 to 25 can optionally include the impact piston having a distal circumferential ridge to engage a reverse impact cap to generate reserve impacts.

In Example 27, the subject matter of any one of Examples 22 to 26 can optionally include the impact assembly having an impact button adapted to receive impacts from the impact hammer.

In Example 28, the subject matter of Example 27 can optionally include the impact assembly having an impact interface adapted to transfer impacts received on the impact button to an impact tool held in a chuck adjacent a distal end of the impact tool.

In Example 29, the subject matter of any one of Examples 27 or 28 can optionally include the impact button being a polymer material and the impact hammer is a dense metal.

In Example 30, the subject matter of any one of Examples 27 to 29 can optionally include the impact button having a pocket formed to receive a radiused proximal surface of the impact hammer.

In Example 31, the subject matter of any one of Examples 22 to 30 can optionally include a proximal bias spring and a distal bias spring that operate to center the shuttle within the house and absorb excess impact energy.

In Example 32, the subject matter of any one of Examples 22 to 32 can optionally include a proximal energy absorption assembly and a distal energy absorption assembly.

In Example 33, the subject matter of Example 32 can optionally include the proximal energy absorption assembly having a forward absorption ring and a proximal bias ring.

In Example 34, the subject matter of Example 33 can optionally include the forward absorption ring being an energy absorbing rubber and the proximal bias ring being a metallic ring structure adapted to receive the proximal bias spring.

In Example 35, the subject matter of any one of Examples 22 to 34 can optionally include an impact shaft transmits impact from the impact assembly and extends distally through an impact shaft bearing assembly, the impact shaft bearing assembly operating as a self-aligning shaft bearing on the impact shaft.

In Example 36, the subject matter of any one of Examples 22 to 35 can optionally include a position sensor assembly including a slider clip to removably couple a position slider to the shuttle.

Example 37 is a method for homing any one of the impact tools of Examples 1 to 36. The homing method can include: operating a linear electric motor to reverse a shuttle mechanism to a distal hard stop; monitoring a position sensor assembly during operation of the linear electric motor; determining, based on feedback from the position sensor assembly and the linear electric motor, that a distal home position has been reached; upon determining that the distal home position was reached, operating the linear electric motor to move the shuttle mechanism to a proximal home position; and determining, based on feedback from the position sensor and the linear electric motor, that the proximal home position has been reached.

In Example 38, the subject matter of Example 37 can optionally include the determining the distal home position has been reached by monitoring voltages on a distal position sensor and a proximal position sensor.

In Example 39, the subject matter of any one of Examples 37 and 38 can optionally include calibrating the sensor assembly based on voltage readings at the distal home and proximal home positions.

Example 40 is a method of operating any one of the impact tools of Examples 1 to 36. The operating method can include: detecting activation of a trigger mechanism to initiate an impact from the impact tool; determining a position of a shuttle assembly within a housing of the impact tool, the shuttle including components adapted to generate an impact; determining, from the position of the shuttle assembly, an intended impact direction; and delivering an impact in the intended impact direction by operating a linear electric impact mechanism.

In Example 41, the subject matter of Example 40 can optionally include after delivering the impact, determining, based on a position of the trigger mechanism, whether to repeat delivery of the impact.

In Example 42, the subject matter of Example 41 can optionally include upon determining not to repeat delivery of the impact, parking the linear electric impact mechanism.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Figure 1A:
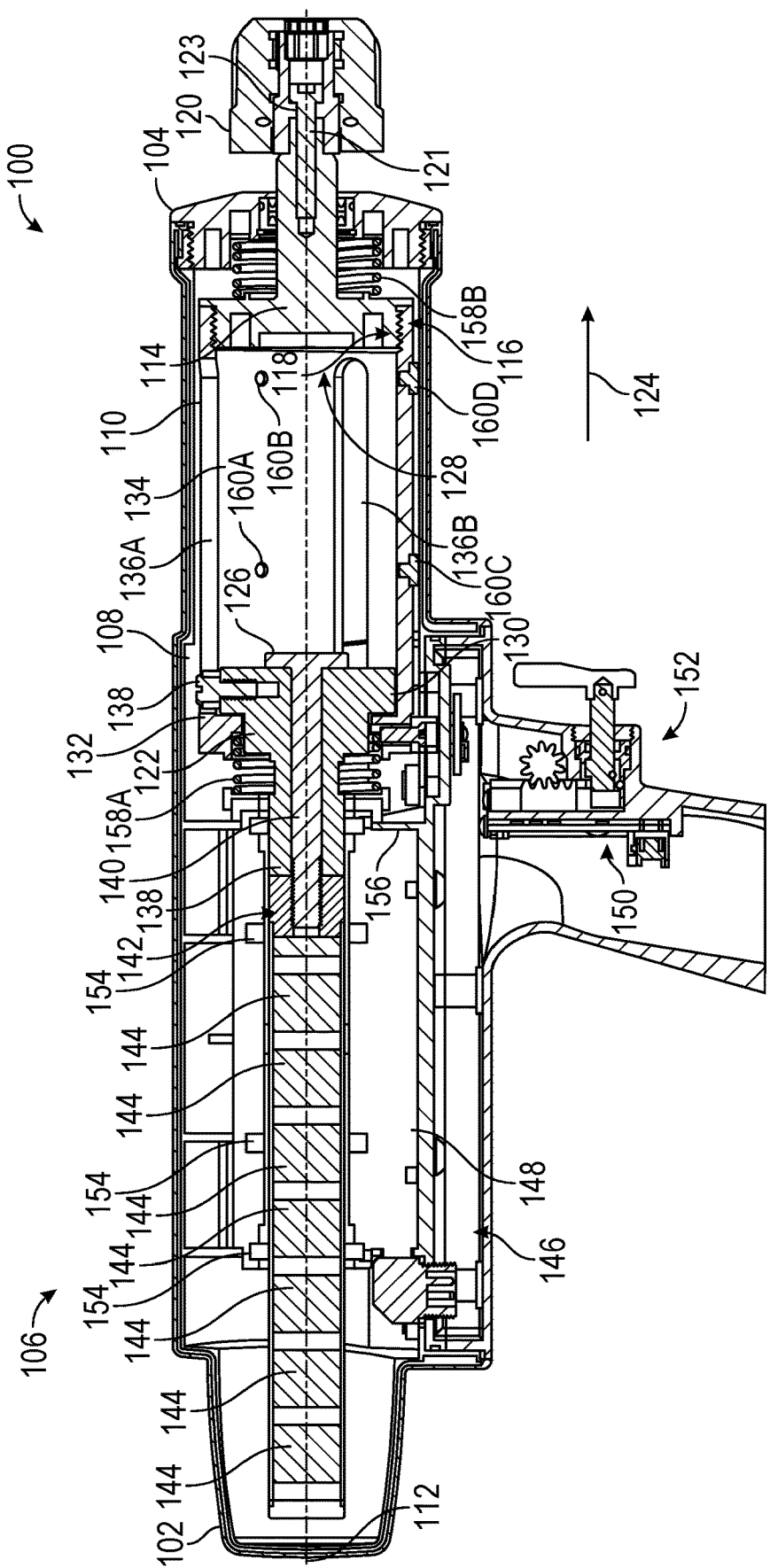
FIGS. 1A and 1B each shows section view of a linear electric surgical hammer impact tool consistent with at least one example of this disclosure.

Corresponding reference characters indicate corresponding parts throughout the several views. The exemplifications set out herein illustrate exemplary embodiments of the disclosure, and such exemplifications are not to be construed as limiting the scope of the disclosure in any manner. Reference characters used in FIGS. 3-9C do not necessarily have any correspondence to reference characters used in previous figures.

DETAILED DESCRIPTION

As an alternative to a pneumatic piston driven system, disclosed herein are electrically driven systems. Specifically, the linear electric surgical hammer impact tools disclosed herein can include impact elements, sometimes called sliders that can impact shuttles, tool holding elements, etc. to generate impact forces.

An electric motor can be configured to drive the impact elements to create the impact forces. For example, motion of a piston in a first direction can cause the piston to contact a first end of a housing and motion of the piston in a second direction can cause the piston to contact a second end of the housing. The contact between the piston and the housing can generate the impact forces to drive a rasp and/or broach into a canal of a bone and extract the rasp and/or broach from the canal.

The above discussion is intended to provide an overview of subject matter of the present patent application. It is not intended to provide an exclusive or exhaustive explanation of the invention. The description below is included to provide further information about the present patent application.

Figure 1B:
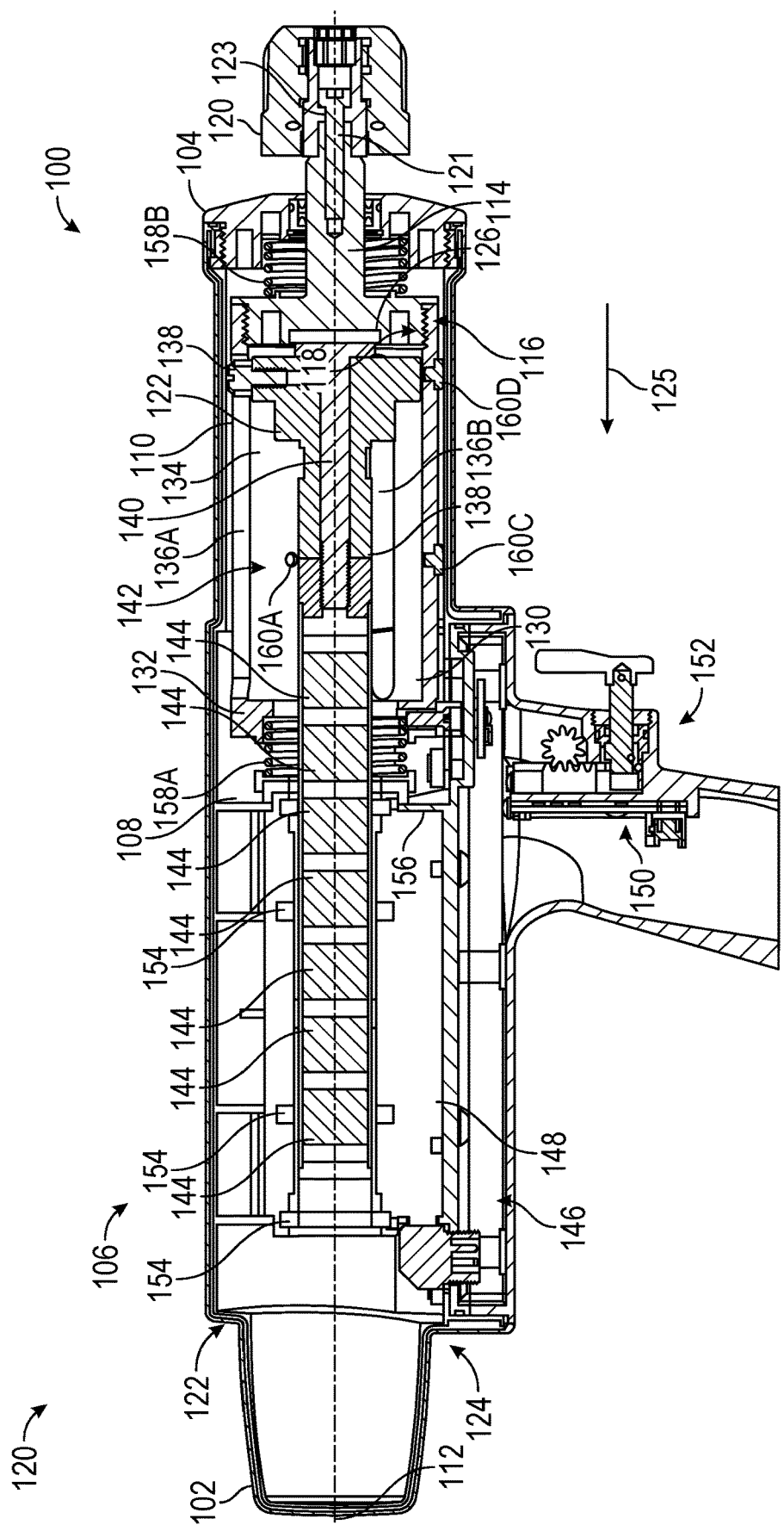

Turning now to the figures, FIGS. 1A and 1B each shows an example of a linear electric surgical hammer impact tool 100 consistent with at least one example of this disclosure. As disclosed herein, linear electric surgical hammer impact tool 100 can provide a simple, efficient, and robust battery powered handheld linear electric surgical hammer impact tool for use in surgical procedures. Linear electric surgical hammer impact tool 100 can include a distal end cap 102 and a proximal end cap 104 on opposite ends of a housing 106. Housing 106 can sometimes be referred to as a tool body and can define a cavity 108.

A shuttle 110 can be located within cavity 108 and arranged along a longitudinal axis 112 of housing 106. A tool holder 114 can be connected to shuttle 110. For example, and as shown in FIGS. 1A and 1B, shuttle 110 can include first threads 116 and shuttle 110 can have second threads 118 that allow tool holder 114 to be threadably connected to shuttle 110. Other forms of attaching tool holder 114 to shuttle 110 can include adhesives, press fit, welding, screws, etc.

Tools, such as a rasp, broach, etc., can be attached directed to tool holder 114. For example, a broach can be secured to tool holder 114 via a pin, threads, etc. Consistent with embodiments disclosed herein, a chuck 120 can be attached to tool holder 114. Chuck 120 can be a quick connect/disconnect chuck that allows for a surgeon or other operating room staff to quickly connect and disconnect tools from linear electric surgical hammer impact tool 100. For example, chuck 120 can allow a surgeon to quickly disconnect a first rasp from linear electric surgical hammer impact tool 100 and quickly connect a second rasp, which can be a different size and/or shape than the first rasp, to linear electric surgical hammer impact tool 100.

Chuck 120 can be attached to tool holder 114 via a bolt 121. For example, chuck 120 can define a through hole 123. Bolt 121 can pass through through hold 123 to secure chuck 120 to tool holder 114. The us of bolt 121 can allow a surgeon or other staff to change chucks depending on a surgeon's preference. For instance, a first surgeon can prefer a first type of chuck and a second surgeon can prefer a second type of chuck. Use of bolt 121 can allow staff to change chucks in between surgery performed by the first and second surgeons.

Linear electric surgical hammer impact tool 100 can further include a piston 122 located at least partially within housing 106. During operation, piston 122 can move in a first direction as indicated by arrow 124 (FIG. 1A). Motion in the first direction can cause a surface 126 of piston 122 to contact a surface 128 of shuttle 110 to generate an impact force to drive a tool into bone. Surface 128 of shuttle 110 can be a surface, sometimes called an impact surface, of tool holder 114.

Motion of piston 122 in a second direction as indicated by arrow 125 (FIG. 1B) can cause a flange 130 of piston 122 to impact a distal portion 132 of shuttle 110. The impact of flange 130 with distal portion 132 can generate an extraction force that can allow for tools, such as broaches, rasps, etc. to be removed from bone.

Piston 122 can be constructed from dense materials to increase the impact forces generated. For example, piston 122 can be constructed of a metal, such a tungsten, that includes more mass for a given volume of material. The result is that for a given velocity, piston 122 can have a greater kinetic energy that can be transferred to tool holder 114 and/or shuttle 110 via piston 122 impacting tool holder 114 and/or shuttle 110 as disclosed herein.

Shuttle 114 can include a wall 134. Wall 134 can define grooves 136 (labeled individually as grooves 136A and 136B). Piston 122 can include one or more protrusions 138 that fit within a respect one of grooves 136. Protrusions 138 can act as bearings that secure piston 122 in a particular orientation as well as provide clearance between wall 134 and piston 122 to minimize friction.

Protrusions 138 can be constructed of a polymer. Polymer protrusions can be impregnated with a lubricant to further reduce friction and wear. Protrusions 138 can be secured to piston 122 via threads, adhesives, press fit, etc. The threaded interface between tool holder 114 and shuttle 110 can allow piston 122 to be placed within shuttle 110. Once inside shuttle 110, protrusions 138 can be passed through grooves 136 and attached to piston 122 thereby securing piston 122 in a desired orientation.

Piston 122 can comprise two components. For example, piston 122 can include a body portion 138 and a weight 140. Both body portion 138 and weight 140 can be mad of metals, polymers, ceramics, or any combination thereof. For example, weight 140 can be made of a dense metal, such as tungsten, and body portion 138 can be made of a polymer. Weight 140 can be press into body portion 138. Weight 140 can include a threaded portion 142 that can be used to secure piston to a moveable portion, such as magnets 144 of a motor 146.

Motor 146 can be a linear electric motor and can include magnets 144 and a stator 148. Electronics 150 can be electrically couple motor 146 to a trigger 152. During operations, a user can depress trigger 152 to cause linear electric surgical hammer impact tool 100 to generate impact forces to drive a tool into bone and/or retract a tool from bone as disclosed herein.

Sensors 154 can be used to determine a position of piston 122 within shuttle 110. For example, sensors 154 can be Hall effect sensors that can determine magnet flux generated by magnets 144. Based on the magnetic flux, or changes in the magnetic flux, a position of piston 122 can be determined. Based on the position of piston 122, electronics 150 can apply a current to stator 148 to drive piston 122 to generation impaction and retraction forces. For example, motor 146 can be a tubular electromagnetic linear motor with a coil structure, e.g., stator 148, fixed inside the housing 106. The coil structure actuates a magnetic or ferromagnetic mechanical impact motion element, e.g., magnets 144, which are connected to piston 122, to cause motion base on the position of the magnets as determined by the sensors 154.

Housing 106 can include a partition 156. As disclosed herein, shuttle 110 can oscillate in the first direction as indicated by arrow 124 and the second direction as indicated by arrow 125. When piston 122 is not in contact with surface 128 or distal portion 132, shuttle 110 can be biased toward a neutral position by biasing elements 158 (labeled individually as biasing elements 158A and 158B). Biasing elements 158 can be springs (tensions and/or compression), rubber structures, airbags, etc.

During operation, piston 122 can travel in the first direction and strike surface 128. After striking surface 128, biasing element 158B can push tool holder 114 and shuttle 110 in the second direction to reset shuttle for additional impacts as piston 122 repeatedly strikes surface 128. Shuttle 110 can also be biased in the second direction by the user pressing linear electric surgical hammer impact tool 100 against a bone. In this instance biasing element 158A can act as a shock absorber to mitigate shuttle impacting partition 156 after piston 122 strikes surface 128.

Also, during operation piston 122 can travel in the second direction and strike distal portion 132. After striking distal portion 132, biasing element 158A can push shuttle 110 in the first direction to reset shuttle for additional impacts as piston 122 repeatedly strikes distal portion 132. Shuttle 110 can also be biased in the first direction by the user pulling linear electric surgical hammer impact tool 100 away from a bone. In this instance biasing element 158B can act as a shock absorber to mitigate shuttle 110 impacting cap 104 after piston 122 strikes distal portion 132.

Wall 134 can also define holes 160 (labeled individually as holes 160A, 160B, 160C, and 160D. Plug 162 (labeled individually as plugs 162A, 162B, 162C, and 162D) can be inserted into holes 160. Plugs 162 can be polymer plugs that are impregnated with a lubricant. Thus, plugs 162 can provide friction reduction while supporting shuttle 110. Supporting shuttle 110 can act to keep protrusions 138 aligned within grooves 136 to minimize friction and/or binding that could reduce impact forces.

Figure 2:
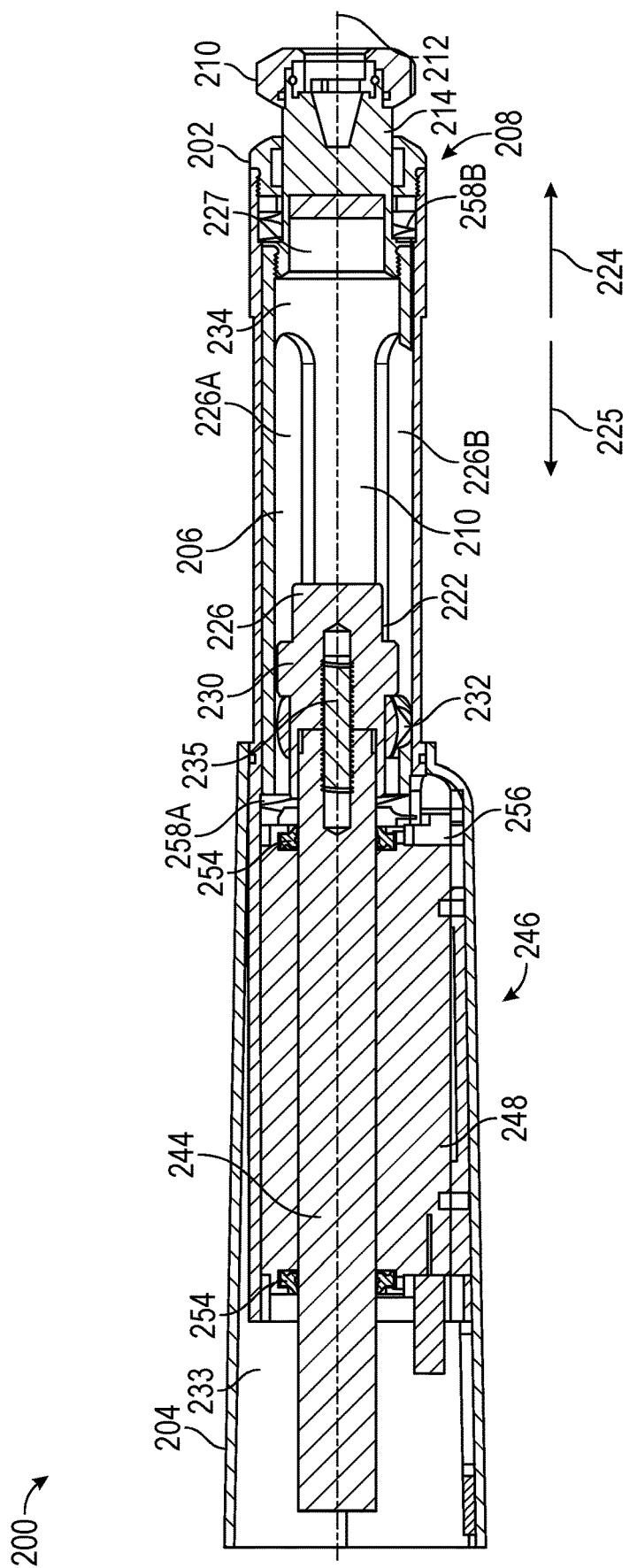
FIG. 2 shows section view of a linear electric surgical hammer impact tool consistent with at least one example of this disclosure.

FIG. 2 shows an example of a linear electric surgical hammer impact tool 200 consistent with at least one example of this disclosure. As disclosed herein, linear electric surgical hammer impact tool 200 can provide a simple, efficient, and robust battery powered handheld linear electric surgical hammer impact tool for use in surgical procedures. Linear electric surgical hammer impact tool 200 can include a distal end cap and a proximal end cap 202 on opposite ends of a housing 204. Housing 204 can sometimes be referred to as a tool body and can define a cavity 206.

A shuttle 210 can be located within cavity 206 and arranged along a longitudinal axis 212 of housing 204. A tool holder 214 can be connected to shuttle 210. For example, and as shown in FIG. 2, a threadable connection 208 can allow tool holder 214 to be threadably connected to shuttle 210. Other forms of attaching tool holder 214 to shuttle 210 can include adhesives, press fit, welding, screws, etc.

Tools, such as a rasp, broach, etc., can be attached directed to tool holder 214. For example, a broach can be secured to tool holder 214 via a pin, threads, etc. Consistent with embodiments disclosed herein, a chuck 220 can be attached to tool holder 214. Chuck 220 can be a quick connect/disconnect chuck that allows for a surgeon or other operating room staff to quickly connect and disconnect tools from linear electric surgical hammer impact tool 200. For example, chuck 220 can allow a surgeon to quickly disconnect a first rasp from linear electric surgical hammer impact tool 200 and quickly connect a second rasp, which can be a different size and/or shape than the first rasp, to linear electric surgical hammer impact tool 200. Chuck 220 can be attached to tool holder 214 via a bolt or other mechanism as disclosed herein with respect to chuck 120.

Linear electric surgical hammer impact tool 200 can further include a piston 222 located at least partially within housing 204. During operation, piston 222 can move in a first direction as indicated by arrow 224. Motion in the first direction can cause a first end 226 of piston 222 to seat within a recess 227 defined by tool holder 214 to generate an impact force to drive a tool into bone.

Motion of piston 222 in a second direction as indicated by arrow 225 can cause a flange 230 of piston 222 to impact a distal portion 232 of shuttle 210. The impact of flange 230 with distal portion 232 can generate an extraction force that can allow for tools, such as broaches, rasps, etc. to be removed from bone.

Piston 222 can be constructed from dense materials to increase the impact forces generated. For example, piston 222 can be constructed of a metal, such a tungsten, that includes more mass for a given volume of material. The result is that for a given velocity, piston 222 can have a greater kinetic energy that can be transferred to tool holder 214 and/or shuttle 210 via piston 222 impacting tool holder 214 and/or shuttle 210 as disclosed herein.

Shuttle 214 can include a wall 234. Wall 234 can define grooves 236 (labeled individually as grooves 236A and 236B). Piston 222 can include one or more protrusions as disclosed herein with respect to protrusions 138 that fit within a respect one of grooves 236 and act as bearings that secure piston 222 in a particular orientation as well as provide clearance between wall 234 and piston 222 to minimize friction. The protrusions can be constructed of polymers that are impregnated with lubricants and connected to piston 222 as disclosed herein.

Piston 222 can be connected to a slider element 233 via a connecting member 235. Connecting member 235 can be a threaded rod, a rod press fitted into both slider element 233 and piston 222, welded to slider element 233, and/or via adhesives. Piston 222 can include weights and can be multiple components as disclosed with respect to piston 122.

Slider element 233 can be a portion of a motor 246, which can be a linear electric motor and can include magnets 244 and a stator 248. As disclosed herein, electronics can be electrically couple motor 246 to a trigger. During operations, a user can depress the trigger to cause linear electric surgical hammer impact tool 200 to generate impact forces to drive a tool into bone and/or retract a tool from bone as disclosed herein.

Sensors 254 can be used to determine a position of piston 222 within shuttle 210. For example, sensors 254 can be Hall effect sensors that can determine magnet flux generated by magnets 244. Based on the magnetic flux, or changes in the magnetic flux, a position of piston 222 can be determined. Based on the position of piston 222, the electronics can apply a current to stator 248 to drive piston 222 to generation impaction and retraction forces. For example, motor 246 can be a tubular electromagnetic linear motor with a coil structure, e.g., stator 248, fixed inside the housing 204. The coil structure actuates a magnetic or ferromagnetic mechanical impact motion element, e.g., magnets 244, which are connected to piston 222, to cause motion base on the position of the magnets as determined by the sensors 254.

Housing 204 can include a partition 256. As disclosed herein, shuttle 210 can oscillate in the first direction as indicated by arrow 224 and the second direction as indicated by arrow 225. When piston 222 is not in contact with tool holder 214 or distal portion 232, shuttle 210 can be biased toward a neutral position by biasing elements 258 (labeled individually as biasing elements 258A and 258B). Biasing elements 258 can be springs (tensions and/or compression), rubber structures, airbags, etc.

During operation, piston 222 can travel in the first direction and strike tool holder 214. After striking tool holder 214, biasing element 258B can push tool holder 214 and shuttle 210 in the second direction to reset shuttle for additional impacts as piston 222 repeatedly strikes tool holder 214. Shuttle 210 can also be biased in the second direction by the user pressing linear electric surgical hammer impact tool 200 against a bone. In this instance biasing element 258A can act as a shock absorber to mitigate shuttle 210 impacting partition 256 after piston 222 strikes tool holder 214.

Also, during operation piston 222 can travel in the second direction and strike distal portion 232. After striking distal portion 232, biasing element 258A can push shuttle 210 in the first direction to reset shuttle for additional impacts as piston 222 repeatedly strikes distal portion 232. Shuttle 210 can also be biased in the first direction by the user pulling linear electric surgical hammer impact tool 200 away from a bone. In this instance biasing element 258B can act as a shock absorber to mitigate shuttle impacting cap 202 after piston 222 strikes distal portion 232.

The following describes an additional embodiment of an impact instrument designed for using in orthopedic joint replacement procedures, among other surgical procedures. The impact instrument described below is another instrument that utilizes a linear electric motor to drive a hammer assembly within a shuttle structure to produce forward and/or reverse impacts on an attached instrument, such as a broach or rasp. As with the tool described above, an electric motor can be configured to drive the impact elements to create the impact forces. The following description focused on areas where this example impact instrument differs from the device described above. The basic operational characteristics are similar between the two examples, as they both utilize a similar linear electric motor to drive the hammer assembly to create impact forces at an attached impact instrument, such as a broach or rasp.

Figure 3:
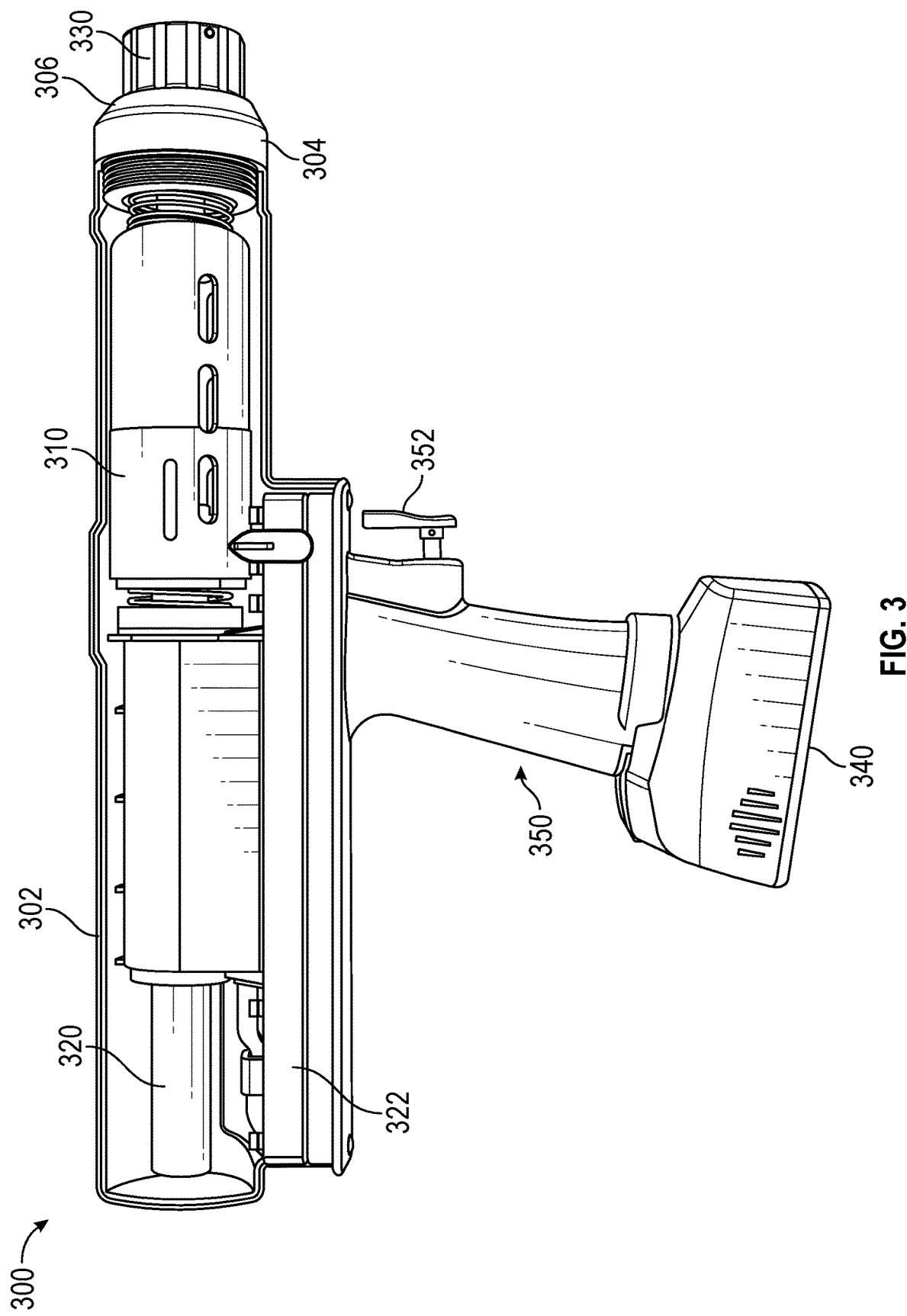
FIG. 3 is a cut away view of a linear electric impact tool consistent with at least one example of this disclosure.

FIG. 3 is a cut away view of a linear electric impact tool 300 consistent with at least one example of this disclosure. In this example, the impact tool 300 is illustrated in a partial cut away view with a portion of the housing 302 removed to allow visualization of certain sub-assemblies within the tool. The cut away portion of the housing 302 reveal the shuttle assembly 310 and the linear electric motor assembly 320. The shuttle assembly 310 is the structure that produces the impact forces transferred to an instrument coupled to the chuck 330. The shuttle can include a cylindrical body that contains impact receiving structures on both the distal and proximal ends. The shuttle also retains the impact hammer assembly that is the portion of the impact tool 300 that moves to generate impact forces. The impact hammer assembly is linearly translated by the linear electric motor assembly 320. Details on these sub-assemblies are discussed below in reference to FIGS. 4A-8B.

The impact tool 300 also includes a battery assembly 340 and a handle 350. In this example, the handle 350 includes a trigger 352 for activation of the impact tool 300. The housing 302 also includes a proximal end cap 304 that threads into a proximal end of the housing 302. Adjacent the proximal end cap 304 is a proximal cap seal 306 that seals the proximal end of the impact tool 300.

In this example, the housing 302 of the impact tool 300 is an injection molded plastic or polymer that is laser welded together during the assembly process. The housing 302 is specifically designed to minimize impacts on the motor dynamics of the linear electric motor assembly 320. The use of injection molded plastic was favored over a metal housing, such as aluminum, to avoid eddy current braking effects on the linear electric motor. Another housing material choice that can be used to similarly avoid eddy current impacts would be laminating non-conductive or low conductivity metals to form the housing 302.

Figure 4A:
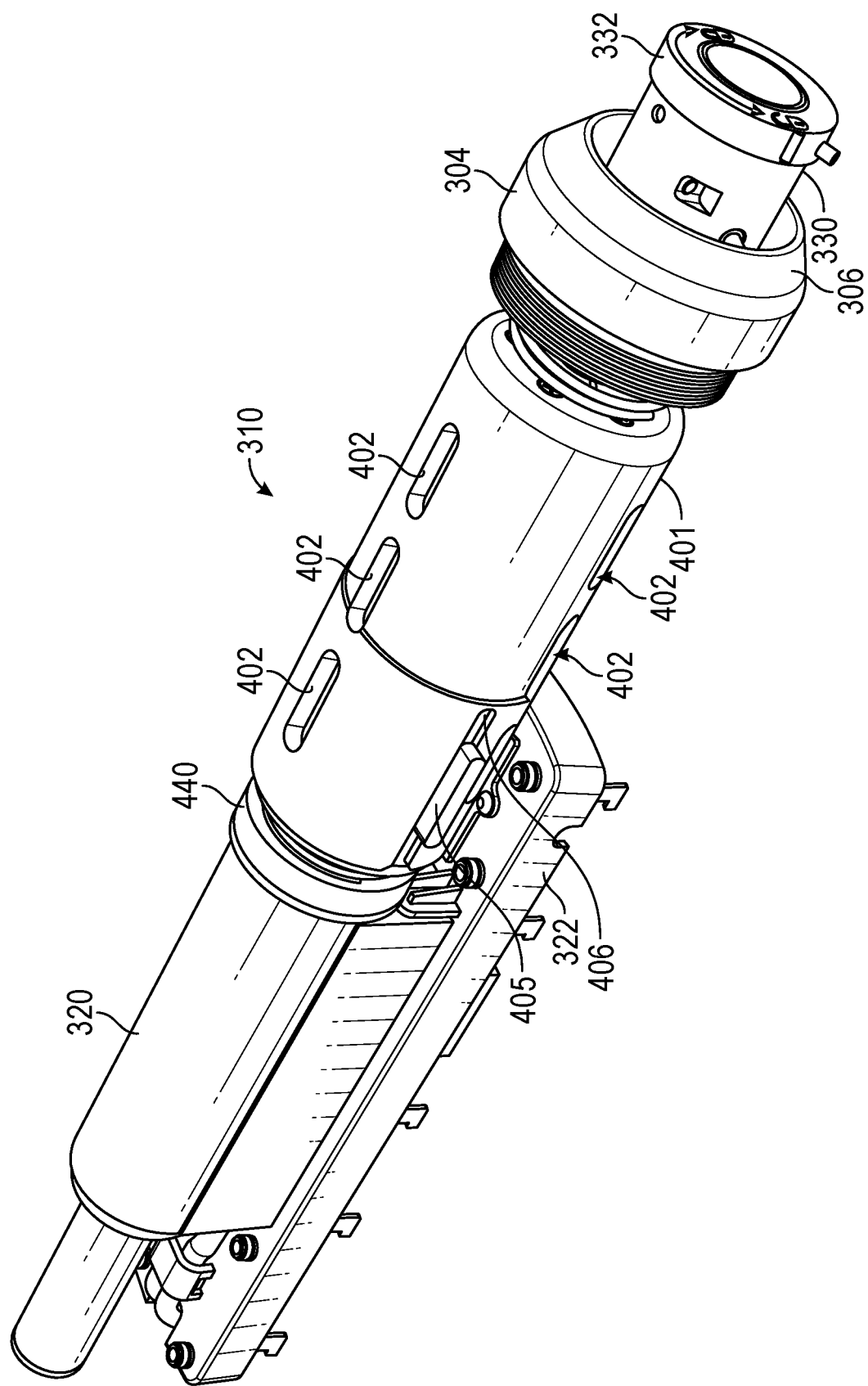
FIG. 4A is a perspective view illustrating multiple sub-assemblies of a linear electric impact tool consistent with at least one example of this disclosure.

FIG. 4A is a perspective view illustrating multiple sub-assemblies of a linear electric impact tool 300 consistent with at least one example of this disclosure. In this example, FIG. 4A illustrates the shuttle assembly 310 and the linear electric motor assembly 320 extracted from the impact tool 300. In this example, the shuttle assembly 310 includes a cylindrical shuttle housing 401 with multiple shuttle vents 402 and at least two opposing key grooves to receive shuttle keys 405. The shuttle vents 402 operate to vent the interior portion of the shuttle housing 401, which reduces air compression induced drag on the hammer assembly 430. The shuttle keys 405 restriction rotation of the shuttle housing 401 relative to the housing 302 of the impact tool 300. The shuttle assembly 310 also includes a distal energy absorption assembly 440 discussed in detail below. The linear electric motor assembly 320 can include control circuit assembly 322 that includes a circuit board containing control electronics for controlling the linear electric motor and providing position feedback regarding the hammer assembly within the shuttle housing 401. The figure also includes illustration of the chuck 330 and chuck lock 332. The chuck lock 332 rotates to lock an impact instrument into the impact tool 300.

Figure 4B:
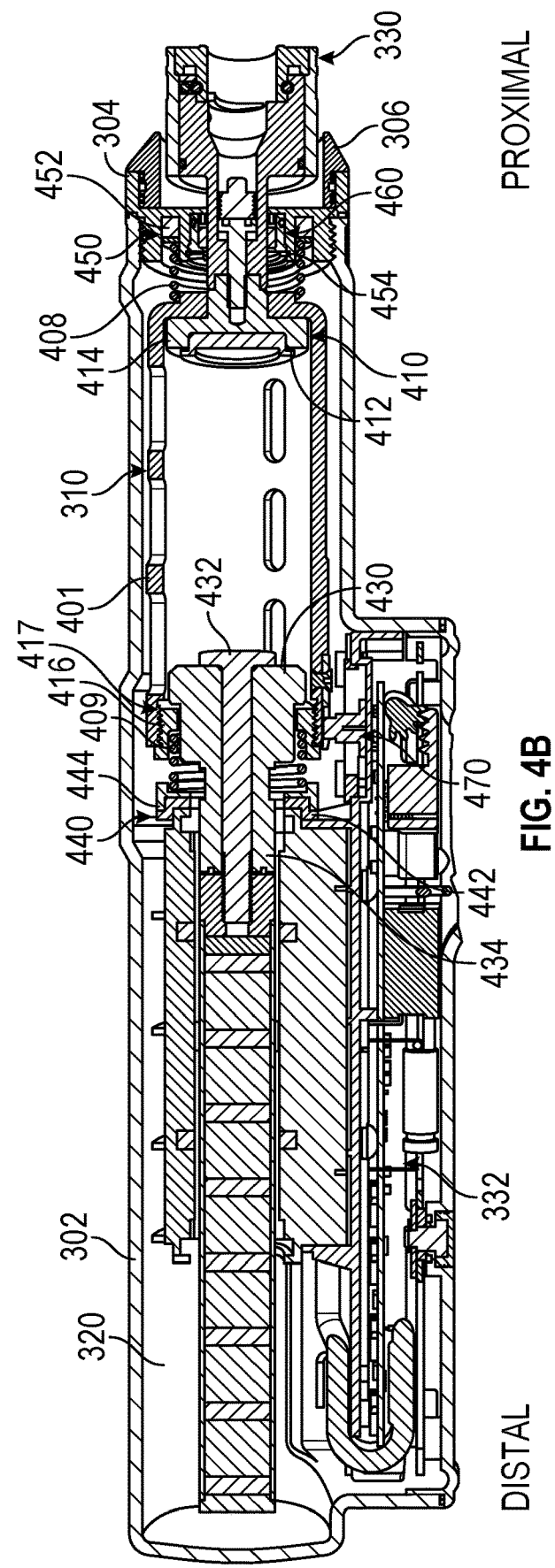
FIG. 4B is a cross section view of multiple sub-assemblies of a linear electric impact tool consistent with at least one example of this disclosure.

FIG. 4B is a cross section view of multiple sub-assemblies of a linear electric impact tool 300 consistent with at least one example of this disclosure. In this example, the sub-assemblies discussed above are illustrated in cross section to detail additional components within each sub-assembly. In this example, the linear electric motor assembly 320 can include the linear electric motor, the control circuit assembly 322 and a position sensor assembly 470. The position sensor assembly 470 includes a structure that clips into the shuttle housing 401 to monitor position of the shuttle assembly 310 during operation. The linear electric motor (discussed in detail above) includes internal sensors to provide feedback on the position of the hammer assembly 430.

In this example, the shuttle assembly 310 includes the shuttle housing 401, an impact assembly 410, the hammer assembly 430, the distal energy absorption assembly 440, the proximal energy absorption assembly 450, and the impact shaft bearing assembly 460. The impact assembly 410 can include an impact button 412 and an impact interface 414. The impact button 412 is for receiving forward impacts from the impact hammer 432. In order to minimize energy loss due to vibrations, the impact button 412 can be made of a low-loss polymer material, such as Acetal® or Delrin®. The low-loss polymers have low wear characteristics allowing the impact assembly 410 to provide a long service life. In this example, the impact hammer 432 is part of the hammer assembly 430 that also includes a reverse impact piston 434. The impact button 412 also includes a pocket formed to receive the radiused proximal surface of the impact hammer 432, which further enhances energy transfer between the impact hammer 432 and the impact button 412. The radius of the proximal surface allows the edge of the impact zone of the impact hammer 432 to avoid contact with the surface of the impact button 412. The radius of the proximal surface can be in the range of 10% to 25% of the diameter of the impact button 412 and accomplish the goal of avoiding edge contact. In this example, the impact button 414 is held in a recess within the impact interface 414. The impact interface 414 transfers energy received by the impact button 412 to an impact tool held in the chuck 330. The impact interface 414 includes a proximal shaft extending outside the shuttle housing 401 that interfaces with a distal end of an impact shaft extending distally from the chuck 330. The impact shaft is held in position by an impact shaft bearing assembly 460.

In this example, the impact hammer 432 is a dense metal material to enhance the impact energy transfer to the impact button 412. The combination of the dense metal impact hammer 432 and the stiff polymer impact button 412 operates like a dead blow hammer to efficiently transmit impact forces to an impact instrument coupled to the chuck 330. The other component of the hammer assembly 430 is the reverse impact piston 434, which can also be a dense metal material and is designed to impart reverse (or distal) impacts on the reverse impact cap 416 that is threaded into the distal end of the shuttle housing 401. Similar to the impact button 412, the reverse impact cap 416 can be made from a stiff polymer material to efficiently transmit reverse impact forces to the shuttle housing 401. In certain examples, the reverse impact cap 416 can be made from a metallic material to enhance wear characteristics, while the system relies on the long force path created by the shuttle housing 401 to dampen any vibrations generated during reverse impacts.

In this example, the shuttle assembly 310 also includes a proximal bias spring 408 and a distal bias spring 409 (discussed here collectively as "bias springs"). The bias springs operate to keep the shuttle housing 401 centered within the housing 302 during operation. The bias springs also operate to dissipate excess impact energy not transferred into the impact instrument. In an example, energy dissipation is enhanced by the proximal energy absorption assembly 450 and the distal energy absorption assembly 440 (discussed here collectively as "energy absorption assemblies"). The energy absorption assemblies include additional energy absorbing components to dissipate impact forces in case of a dry fire or a situation where the impact instrument is not fully engaged or otherwise able to absorb the impact energy produced by the tool. The energy absorption assemblies operate to minimize negative force transmission to the housing 302 and ultimately to the user of the impact tool 300. In this example, the distal energy absorption assembly 440 includes a reverse absorption ring 442 and a distal bias ring 444. The reverse adsorption ring 442 can be made from energy absorbing rubber, such as Sorbothane®. The distal bias ring 444 can be a metallic ring that receives bias forces from the distal bias spring 409. The proximal energy absorption assembly 450 can include a forward absorption ring 452 and a proximal bias ring 454. Like the reverse absorption ring 442, the proximal absorption ring 452 can be made from an energy absorbing rubber compound such as Sorbothane®. The proximal bias ring 454 is a metallic ring structure designed to receive the proximal bias spring 408 and protect the proximal absorption ring 452. The distal bias ring 444 and the proximal bias ring 454 also operate to distribute forces from the bias springs as they are compressed by forward or reverse impacts.

The impact shaft bearing assembly 460 operates as a self-aligning shaft bearing on the impact shaft that transmits impacts from the shuttle assembly 310 to the chuck 330. In an example, the impact shaft bearing assembly 460 can include a shaft bearing 462, a bearing housing 464, a housing O-ring 466, a shaft seal 468, and a snap ring 469. The shaft bearing 462 guides the impact shaft and allows linear transverse movements of the impact shaft. The bearing housing 464 and housing O-ring 466 cooperate to create a self-aligning bearing assembly by allowing for minute angular movements of the impact shaft within the impact shaft bearing assembly 460. The shaft seal 468 ensures no contaminates enter into the impact tool 300 via the impact shaft. Finally, the snap ring 469 holds the impact shaft bearing assembly 460 into the proximal end cap 304.

Figure 5A:
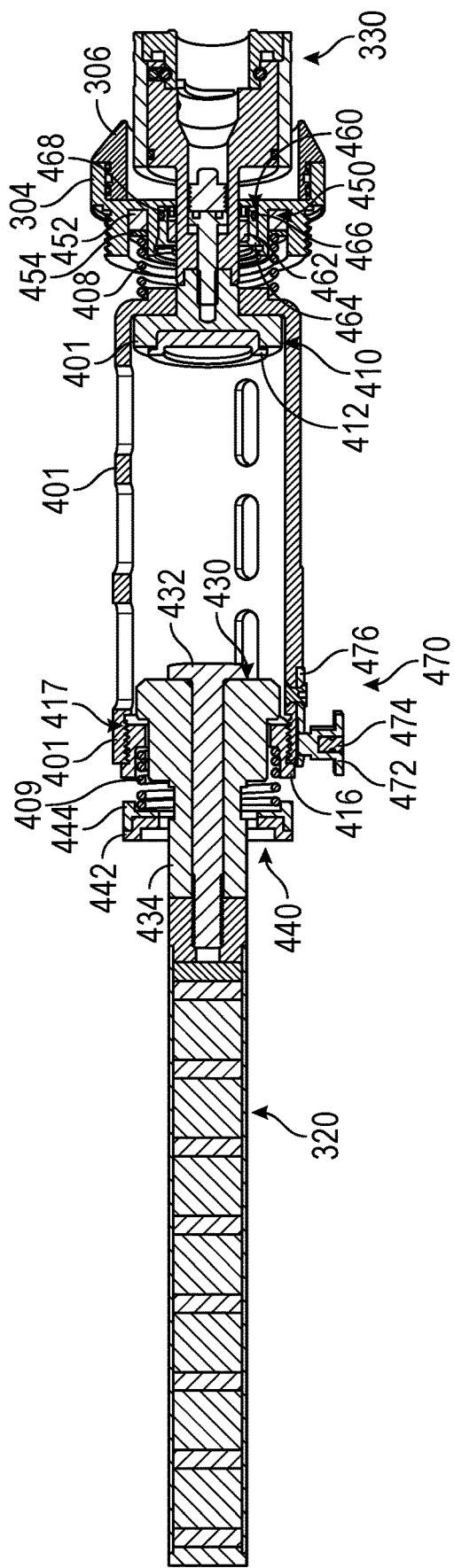
FIG. 5A is a cross section view of multiple sub-assemblies of a linear electric impact tool consistent with at least one example of this disclosure.

FIG. 5A is a cross section view of multiple sub-assemblies of a linear electric impact tool 300 consistent with at least one example of this disclosure. This figure strips away additional housing components of the impact tool 300 to provide for additional detailed views of the shuttle assembly 310 and linear electric motor assembly 320 (note, only the linear electric motor is shown in this figure). The illustrated example includes the impact assembly 410, the hammer assembly 430, the distal energy absorption assembly 440, the proximal energy absorption assembly 450, and the impact shaft bearing assembly 460 as part of the shuttle assembly 310. Components of each of the illustrated assemblies are discussed above. FIG. 5A also includes the position slider 472 and position magnet 474, which are components of the position sensor assembly 470.

Figure 5B:
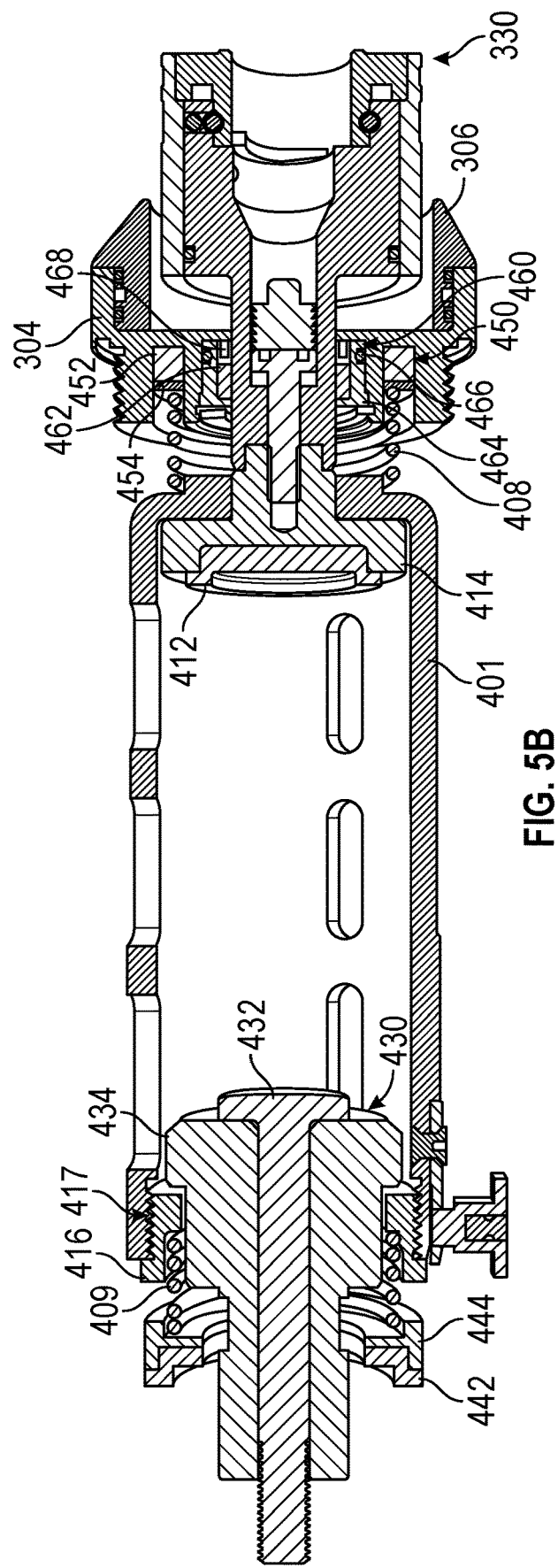
FIG. 5B is a cross section view of an impactor sub-assembly of a linear electric impact tool consistent with at least one example of this disclosure.

FIG. 5B is a cross section view of an impactor sub-assembly of a linear electric impact tool 300 consistent with at least one example of this disclosure. In this example, the impactor sub-assembly corresponds to the shuttle assembly 310 discussed above in reference to FIGS. 4A-5A. In this example, only the shuttle assembly 310 is illustrated with the chuck 330 connected to the impact shaft extending from the impact interface 414. FIG. 5B enables additional detail to be visualized, such as the curvature on the proximal face of the impact hammer 432. In an example, the proximal face of the impact hammer 432 includes a radius of 100 mm. The impact hammer 432 can be milled or cast from metallic materials, such as stainless steel or tungsten.

Figure 6A:
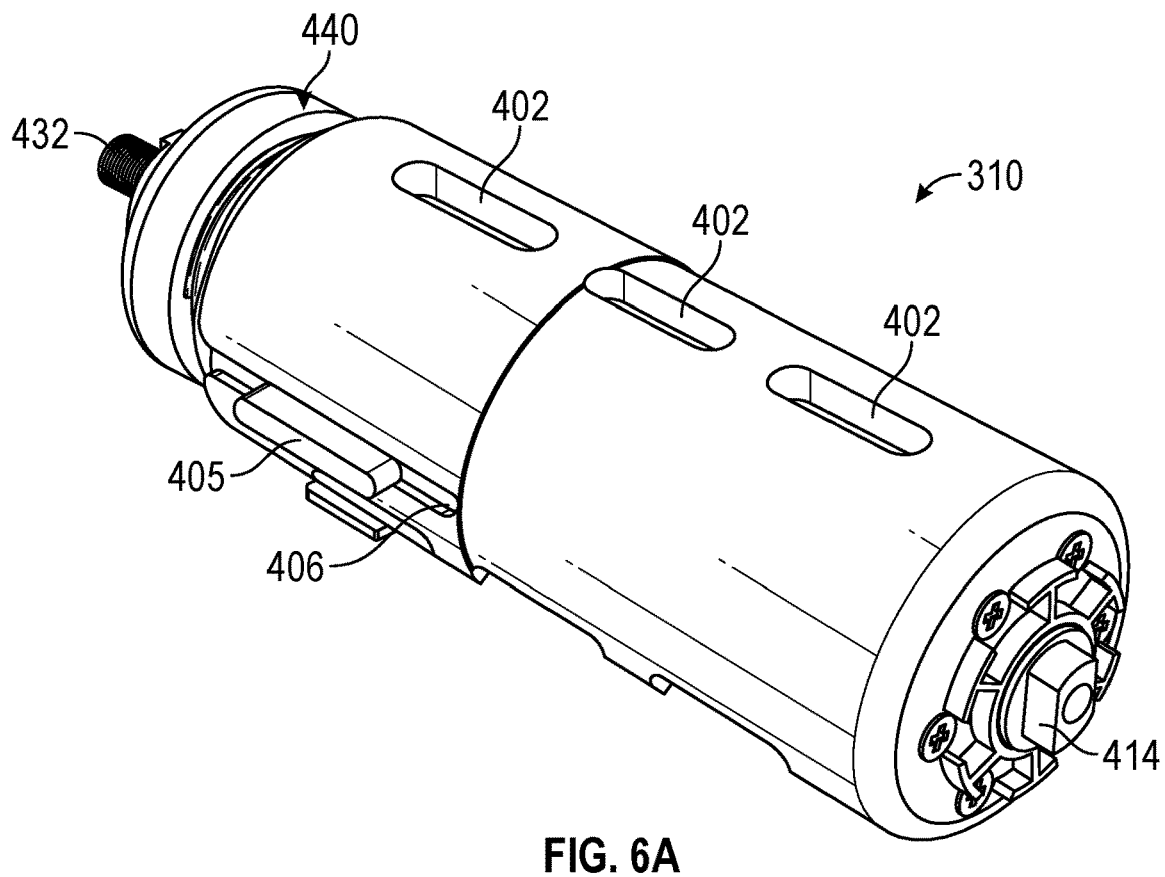
FIGS. 6A-6C are various views of a shuttle sub-assembly of a linear electric impact tool consistent with at least one example of this disclosure.
Figure 6B:
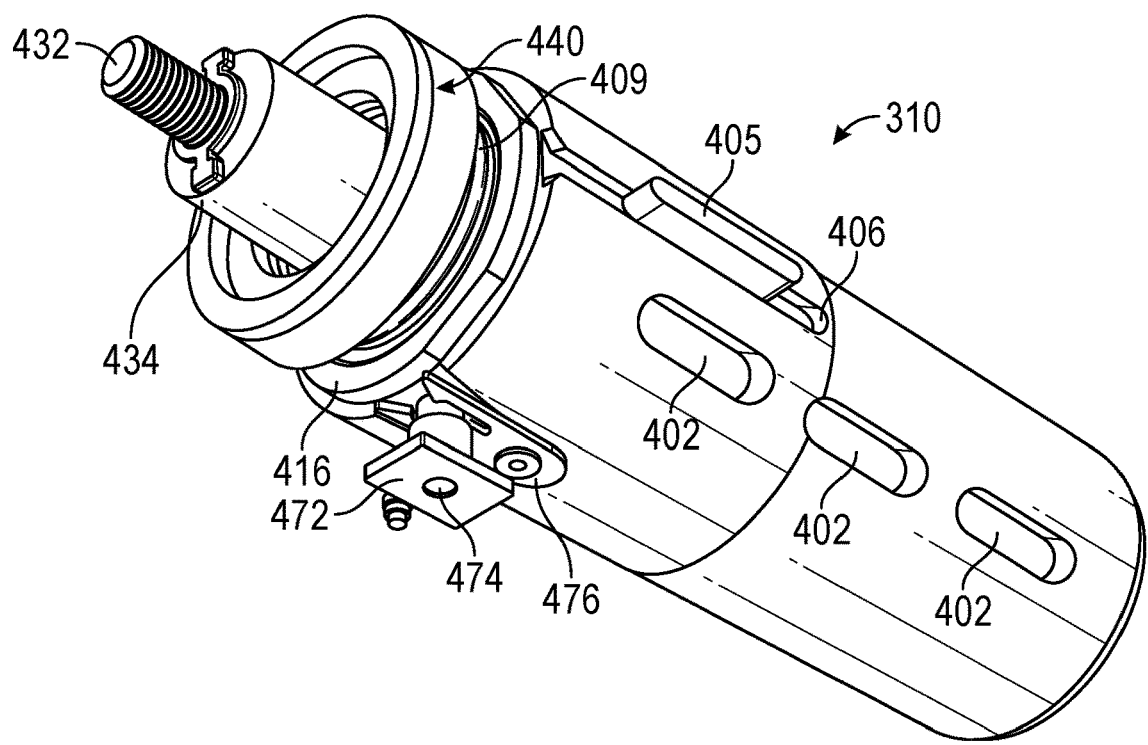
Figure 6C:
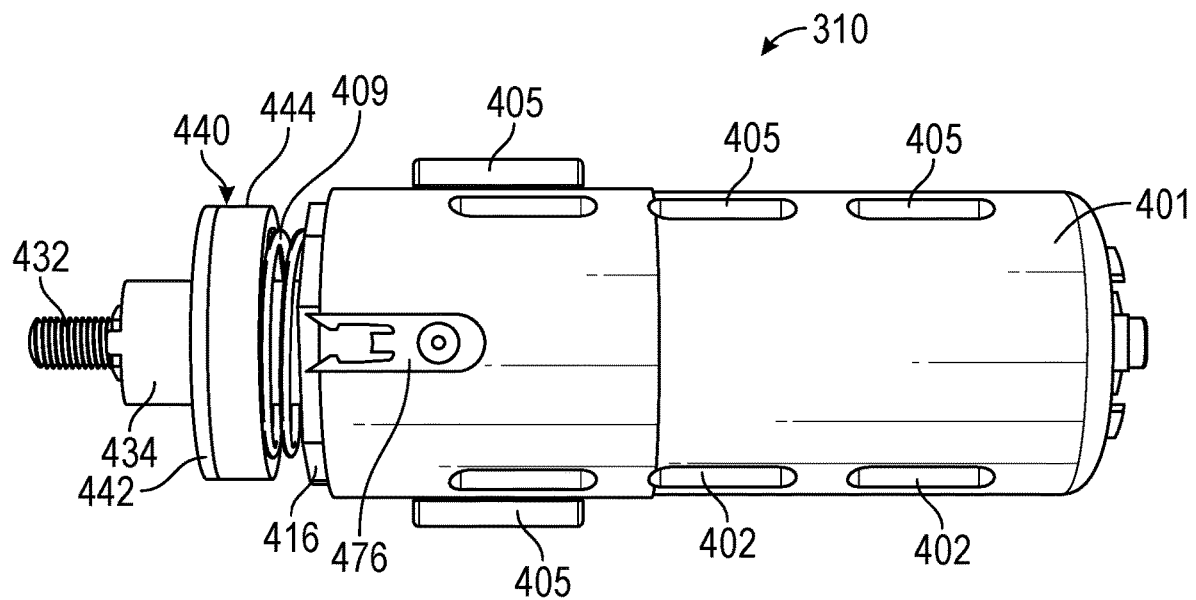

FIGS. 6A-6C are various views of the shuttle sub-assembly 310 of a linear electric impact tool 300 consistent with at least one example of this disclosure. In this example, the shuttle assembly 310 is illustrated extracted from the remainder of the impact tool 300. The shuttle assembly 310 can include a shuttle housing 401, multiple shuttle vents 402, opposing key groove 406 to receive shuttle keys 405. The figures also include components such as distal energy absorption assembly 440 and distal bias spring 409. A threaded end of the impact hammer 432 is shown extending distally from the reverse impact piston 434. In an example, the linear electric motor threads onto the impact hammer 432. On the proximal end of the shuttle housing 401 the proximal end of the impact interface 414 is illustrated. The proximal end of the impact interface 414 receives the impact shaft that couples to the chuck 330.

FIGS. 6B and 6C include illustrations of parts of the position sensor assembly 470 such as the position slider 472, the position magnet 474, and the slider clip 476. The slider clip 476 is the component that couples the position sensor assembly 470 to the shuttle housing 401. More specifically, the slide clip 476 couples to a superior end of the position slider 472 that includes a narrowed cross section to be received into the slide clip 476. The slide clip 476 allows for the shuttle assembly 310 and parts of the linear electric motor assembly 320 to be easily inserted into the tool housing 302 after the electronics and battery are assembled into the housing 302. The slide clip 476 is designed to require a low coupling force due to the angled arms and a high uncoupling force due to the abrupt extensions on the arms. Accordingly, the shuttle and motor assemblies can be easily inserted, while also being possible (but difficult) to remove. The slide clip 476 is designed to release the shuttle assembly 310 if sufficient force is exerted allowing for maintenance or repair of these key components.

Figure 6D:
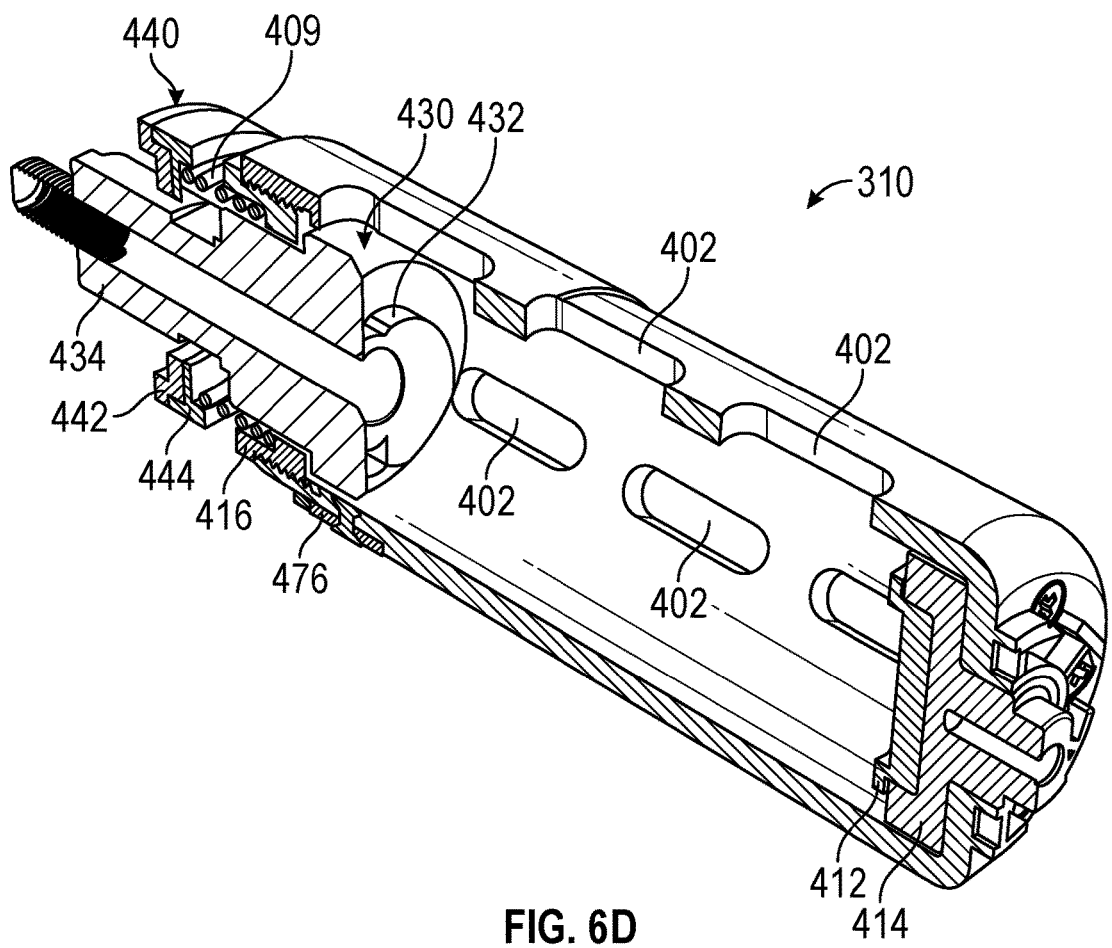
FIG. 6D is a cross section view of a shuttle sub-assembly of a linear electric impact tool consistent with at least one example of this disclosure.

FIG. 6D is a cross section view of the shuttle sub-assembly 310 of a linear electric impact tool 300 consistent with at least one example of this disclosure. This figure is included to provide additional perspective on orientation of different illustrated components. The details of each of the illustrated components is included above.

Figure 7:
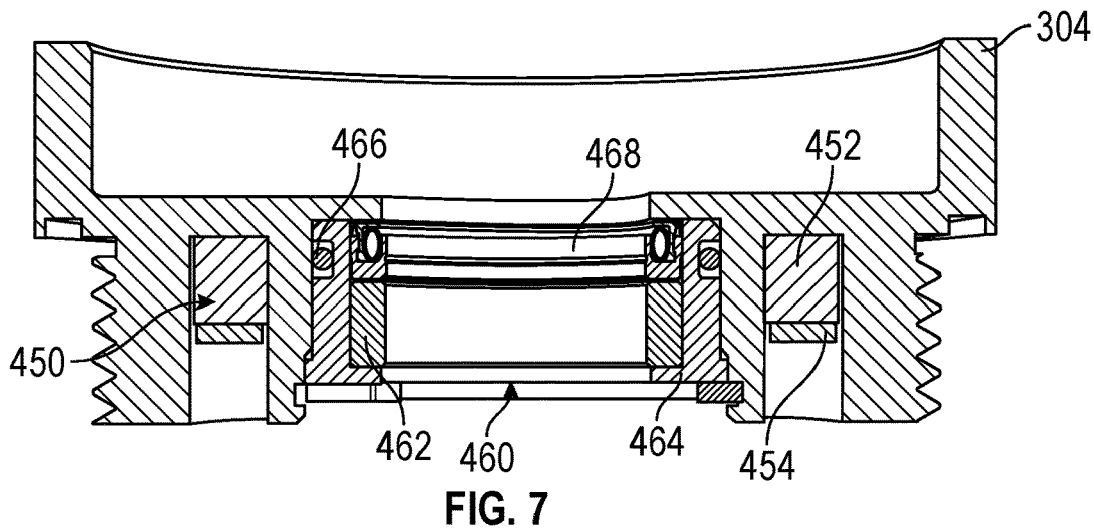
FIG. 7 is a cross section view of a self-aligning impact shaft bearing structure for a linear electric impact tool consistent with at least one example of this disclosure.

FIG. 7 is a cross section view of a self-aligning impact shaft bearing structure for a linear electric impact tool 300 consistent with at least one example of this disclosure. In this example, the impact shaft bearing assembly 460 is illustrated positioned within the proximal end cap 304 of the housing 302. Also included in this illustration is the proximal energy absorption assembly 450 that includes the forward absorption ring 452 and the proximal bias ring 454. The proximal energy absorption assembly 450 is positioned within a deep cylindrical groove in the distal side of the proximal end cap 304. The proximal end cap 304 also includes a central cylindrical bore with a snap ring groove to retain the impact shaft bearing assembly 460. As discussed above, the impact shaft bearing assembly includes the shaft bearing 462, the bearing housing 464, the housing O-ring 466, and the shaft seal 468. In this example, the housing O-ring 466 is depicted within an O-ring groove in the outer surface of the bearing housing 464. The housing O-ring 466 is biased towards the proximal end of the bearing housing 464 in this example. In another example, the housing O-ring 466 can be positioned within an groove centered between the proximal and distal ends of the bearing housing 464. A centered O-ring groove provide different angular self-alignment characteristics. Similarly, the groove could be positioned near the distal end of the bearing housing 464, but this position may have limited angular self-alignment due to the proximity of the snap ring retaining the impact shaft bearing assembly 460.

Figure 8A:
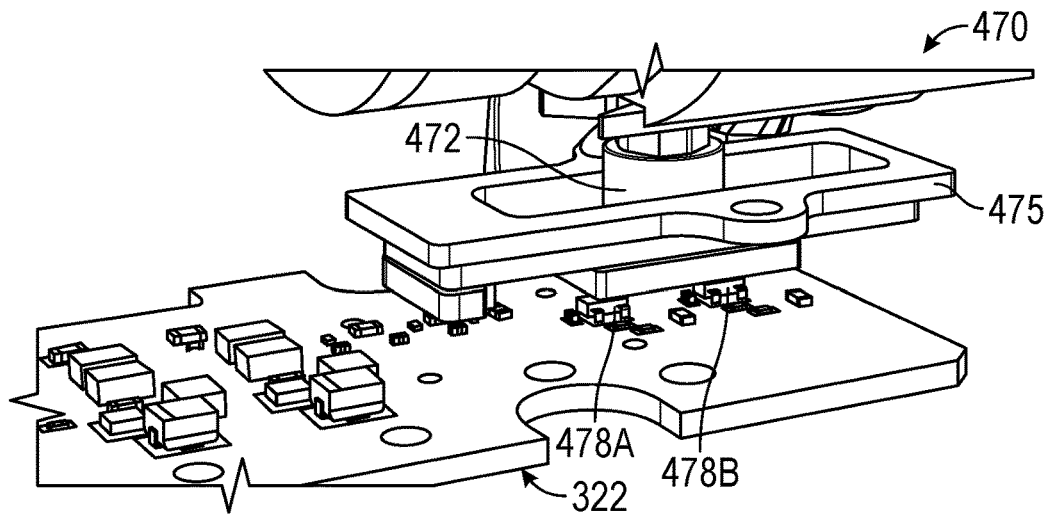
FIGS. 8A-8B are various views of a position sensor sub-assembly for a linear electric impact tool consistent with at least one example of this disclosure.
Figure 8B:
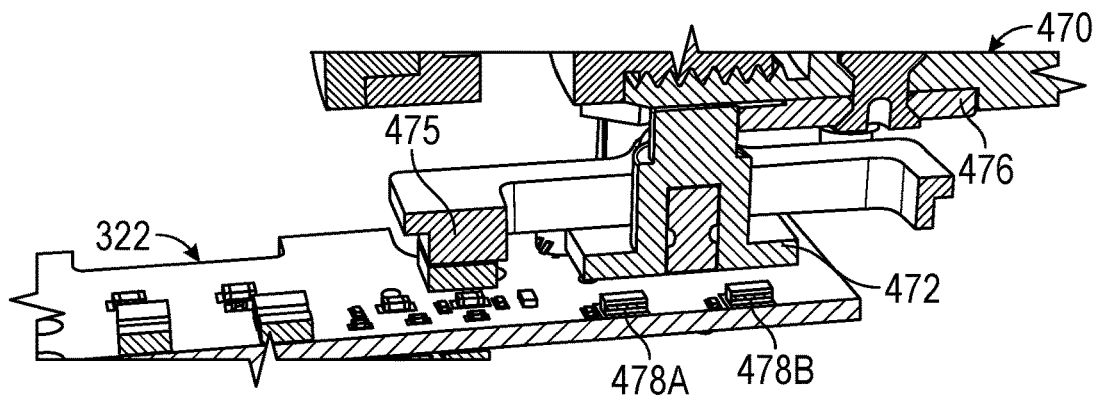

FIGS. 8A-8B are various views of the position sensor sub-assembly 470 for a linear electric impact tool 300 consistent with at least one example of this disclosure. In this example, the position sensor assembly 470 includes the position slider 472, the position magnet 474, the track 475, the slider clip 476 and position sensors 478A, 478B (collectively referenced as position sensors 478). The position slider 472 clips into the slider clip 476 to couple the position slider 472 to the shuttle housing 401. The purpose of the position sensor assembly 470 is to provide position tracking information for the shuttle assembly 310 and more specifically the shuttle housing 401. The position of the shuttle housing 401 is used for a number of control functions including predicting user intent (surgeon intent feature). The impact tool 300 includes control circuitry, including the position sensor assembly 470, to predict user intent regarding forward or reverse impacts. Surgeon intent is discussed in more detail below in reference to the flowchart in FIG. 11.

The position sensor assembly 470 includes two position sensors 478 in order to cover the needed travel distance and to provide both position and directionality of movement. The sensor configuration also allows for on-the-fly calibration as well as tool function verification on start-up (discussed in more detail in reference to FIG. 10 below). In an example, the position sensors 478 are hall-effect sensors. The principle of the "Hall effect" involves a current carrying conductor or semiconductor being introduced to a perpendicular magnetic field, a voltage can be measured at the right angle to the current path. In the present system, the position magnet 474 produces the magnetic field that is then sensed by the position sensors 478, which produce a voltage ranging from 0-3.3 volts. The control circuit assembly 322 includes processing instructions and/or circuitry that combines the output from the two sensors to determine the position of the shuttle housing 401. The processing instructions and/or circuitry can also determine movement direction from the sensor output. Sensor output processing is discussed in greater detail in reference to FIGS. 12A and 12B below.

Figure 9A:
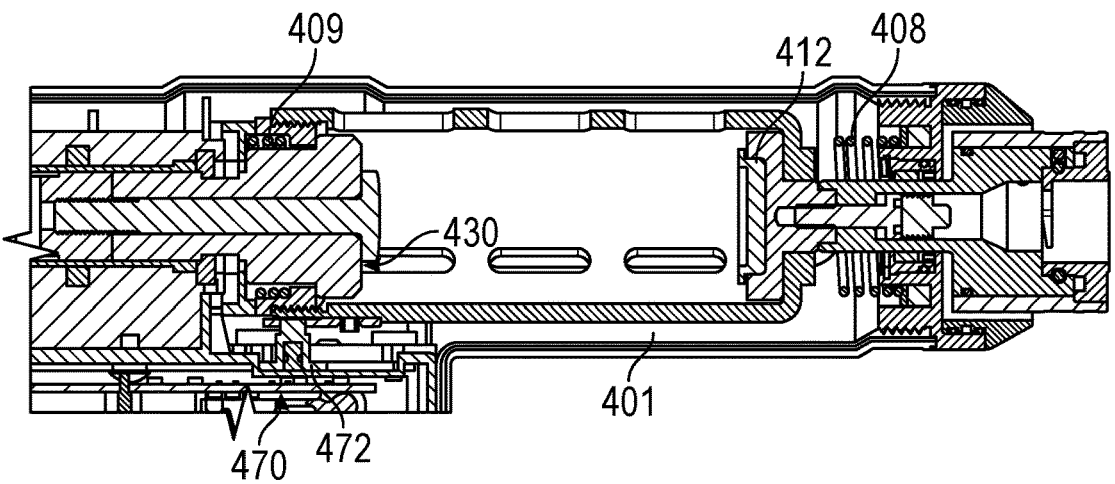
FIGS. 9A-9C are cross section views illustrating various impactor positions within a linear electric impact tool consistent with at least one example of this disclosure.
Figure 9B:
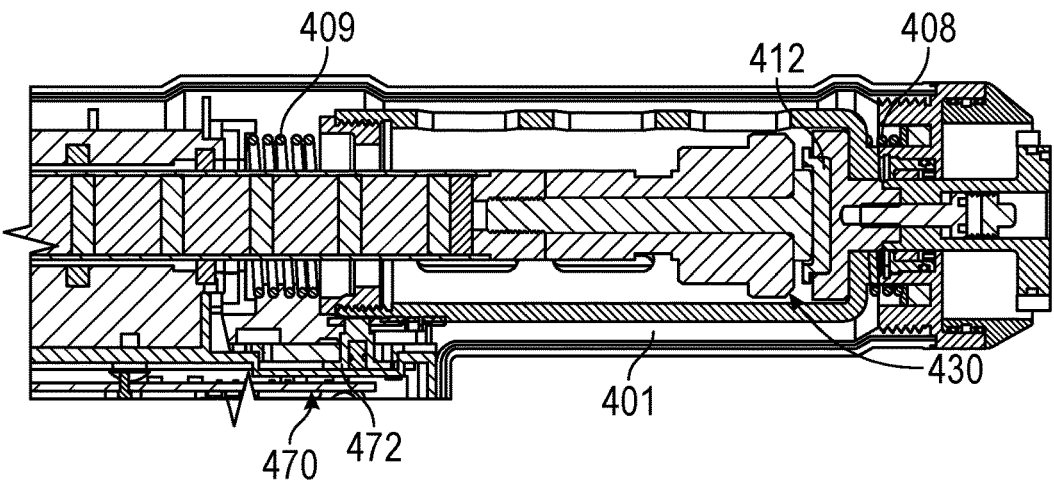
Figure 9C:
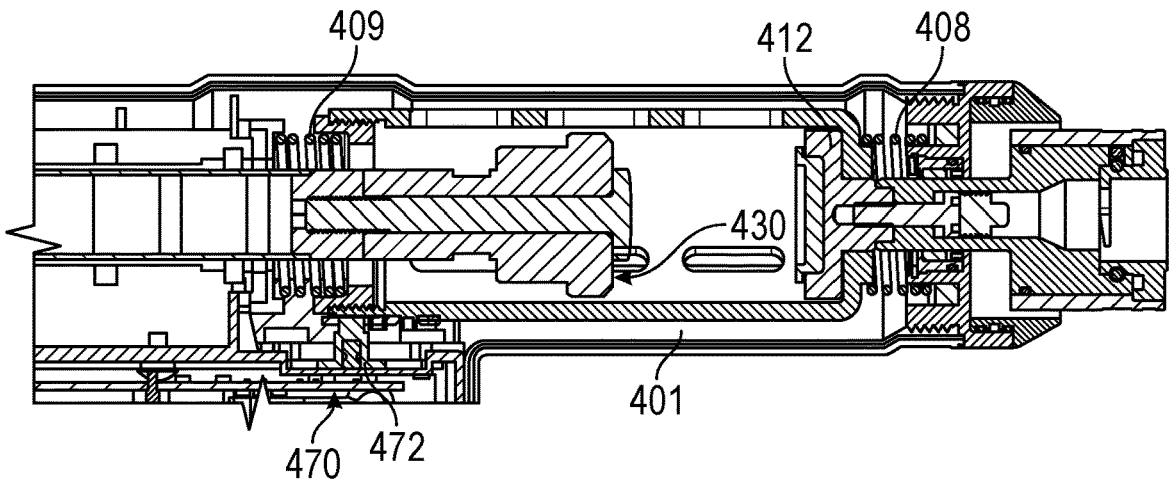

FIGS. 9A-9C are cross section views of the shuttle assembly 310 and parts of the linear electric motor assembly 320 illustrating various hammer assembly 430 positions during operation of the impact tool 300. FIG. 9A illustrates a reverse impact position for the hammer assembly 430. In this position, the hammer assembly 430 is at the distal most position within the impact tool 300. The shuttle housing 401 is compressing the distal bias spring 409 and imparting a reverse impact on any impact instrument attached to the chuck 300. FIG. 9B illustrates the hammer assembly 430 and the shuttle housing 401 in a forward impact position. In the forward impact position, the hammer assembly 430 is impacting the impact button 412 and transmitting impact forces to an impact instrument attached to the chuck 330. The proximal bias spring 408 is fully compressed in this position. FIG. 9C illustrates the impact assembly 430 and the shuttle housing 401 in a neutral position. In the neutral position, both of the bias springs are operating to center the shuttle housing 401. With the hammer assembly 430 parked in a neutral position, such as shown in FIG. 9C, the shuttle housing 401 can be biased distally or proximally by the user pressing down or pulling back on an impact instrument attached to the impact tool 300. The biasing of the shuttle housing 401 and the resulting change in signals from the position sensor assembly is utilized by the control circuit to predict intent of the user (e.g., to predict whether a forward or reverse impact is desired when the trigger is pulled). If a forward impact is intended, the user will push down on the impact instrument, which will bias the shuttle housing 401 distally. Conversely, if a reverse impact is intended, the user will pull back on the impact tool, which will bias the shuttle housing 401 proximally. Of course, this assumes there is some resistance to pulling the impact instrument out to cause the biasing of the shuttle housing 401. The surgeon (user) intent technique is discussed further below in reference to FIG. 11.

Figure 10:
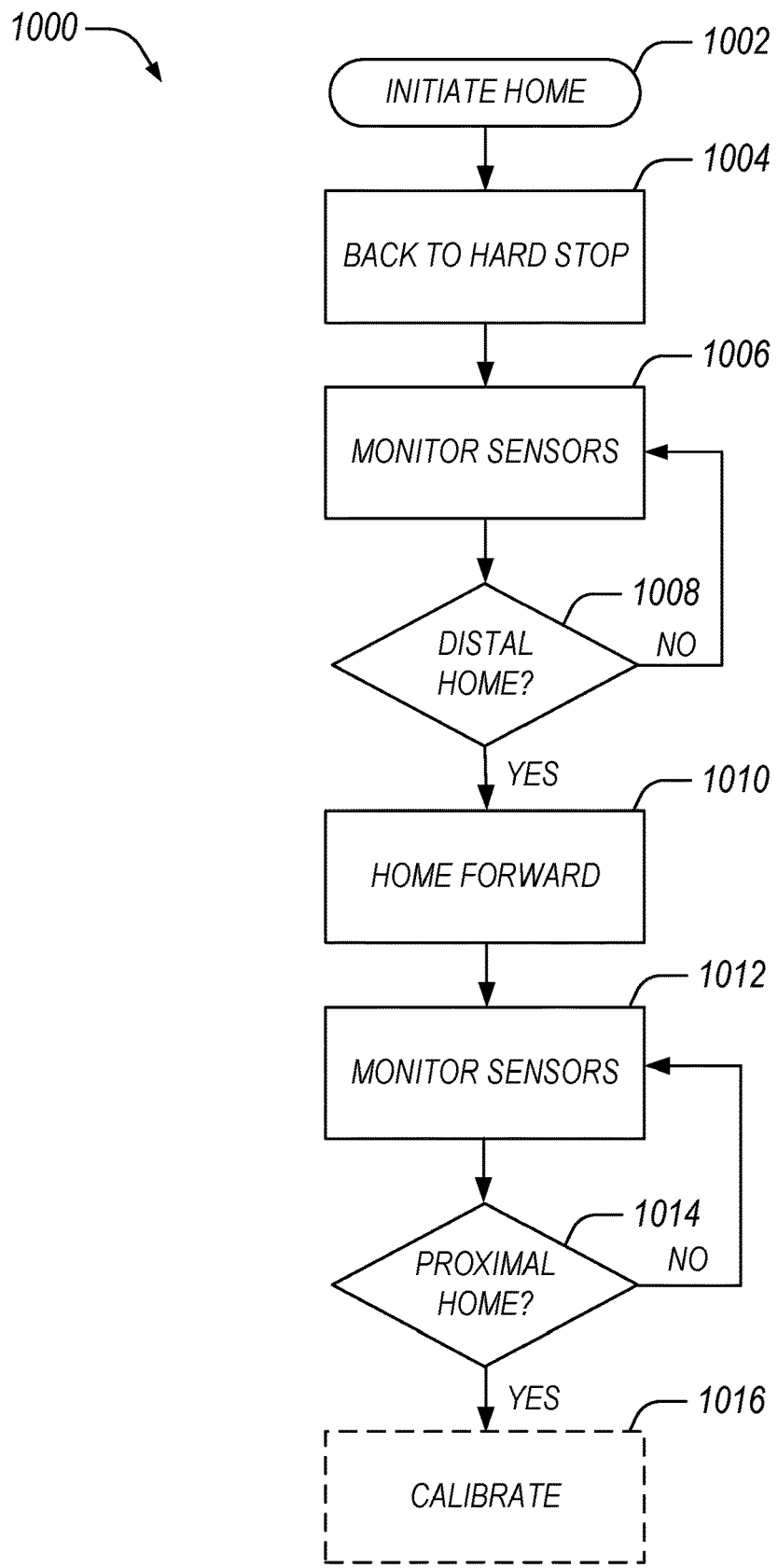
FIG. 10 is a flowchart illustrating a homing and calibration technique for a linear electric impact tool consistent with at least one example of this disclosure.

FIG. 10 is a flowchart illustrating a homing and calibration technique 1000 for a linear electric impact tool consistent with at least one example of this disclosure. In this example, the technique 1000 can include operations such as initiating homing sequence at 1002, backing to a hard stop at 1004, monitoring sensors at 1006, determining if in distal home position at 1008, move to forward home position at 1010, monitoring sensors at 1012, determining if in proximal home position at 1014 and optionally calibrating sensors at 1016.

The technique 1000 can begin at 1002 with the impact tool 300 powering up and initiating a home sequence. The home sequence can be initiated at other times if the control circuitry detects a malfunction or through manual initiation as needed. At 1004, the technique 1000 continues with the linear electric motor assembly 320 moving the hammer assembly 430 in reverse to find a hard stop. During the reserve to hard stop operation, the technique 1000 continues with the control circuitry monitoring sensor outputs at 1006. The control circuitry monitors sensor outputs from the linear electric motor assembly 320 and the position sensor assembly 470. One of the monitored outputs is motor torque, with the control circuitry monitoring for a spike in motor torque that should indicate reaching the reverse hard stop. When the motor torque spike above a pre-defined threshold the position sensors are read to see if the hammer assembly 430 reached the expected reverse hard stop position. In the expected full reverse position, the distal position sensor 478A should be at or near peak voltage of 3.3 volts and the proximal position sensor 478B should be below a pre-defined threshold, such as below 2.5 volts or below 1.25 volts. The thresholds used in these algorithms can be adjusted during calibration. At 1008, the technique 1000 continues with the control circuitry determining if the motor torque and sensor output readings indicate that the motor and hammer assembly 430 reached the reverse hard stop position (e.g., distal home), if confirmed the technique 1000 continues to operation 1010. If not, the technique 1000 loops back to operation 1006 and the control circuitry continues to monitor the sensors back at 1006.

At 1010, the technique 1000 continues with the linear electric motor assembly 320 slowly moving the hammer assembly 430 forward to a proximal home position (where the proximal end of the tool includes the impact instrument). At 1012, the technique 1000 continues with the control circuitry monitoring sensor outputs while the motor moves the hammer assembly 430 to the proximal home position. The sensor outputs monitored at 1012 can include motor torque, distance traveled, and the position sensors 478 (in particular the proximal position sensor 478B). At 1014, the technique 1000 continues with the control circuitry determining whether the proximal home position has been reached. Indications of the hammer assembly 430 reaching the proximal home position can include distance traveled (as measured by the linear electric motor assembly 320), sensing a motor torque peak, and sensing a peak in the proximal position sensor 478B. If the pre-defined parameters are met, the technique 1000 can continue to optionally calibrate the position sensors at 1016. If the parameters are not met, then the technique 1000 loops back to operation 1012 and the control circuitry continues to monitor sensor outputs. At 1016, the technique 1000 can conclude with the control circuitry using the position sensor outputs at the distal and proximal home positions to calibrate the output of the position sensors 478. During the various homing maneuvers the control circuitry can collect the range of output (maximum voltage and minimum voltage) from each sensor. From the minimum and maximum voltage values, the control circuitry captures the offset and range of each sensor, which then allows the control circuitry to calibrate an offset and gain for each sensor based on this data.

Figure 11:
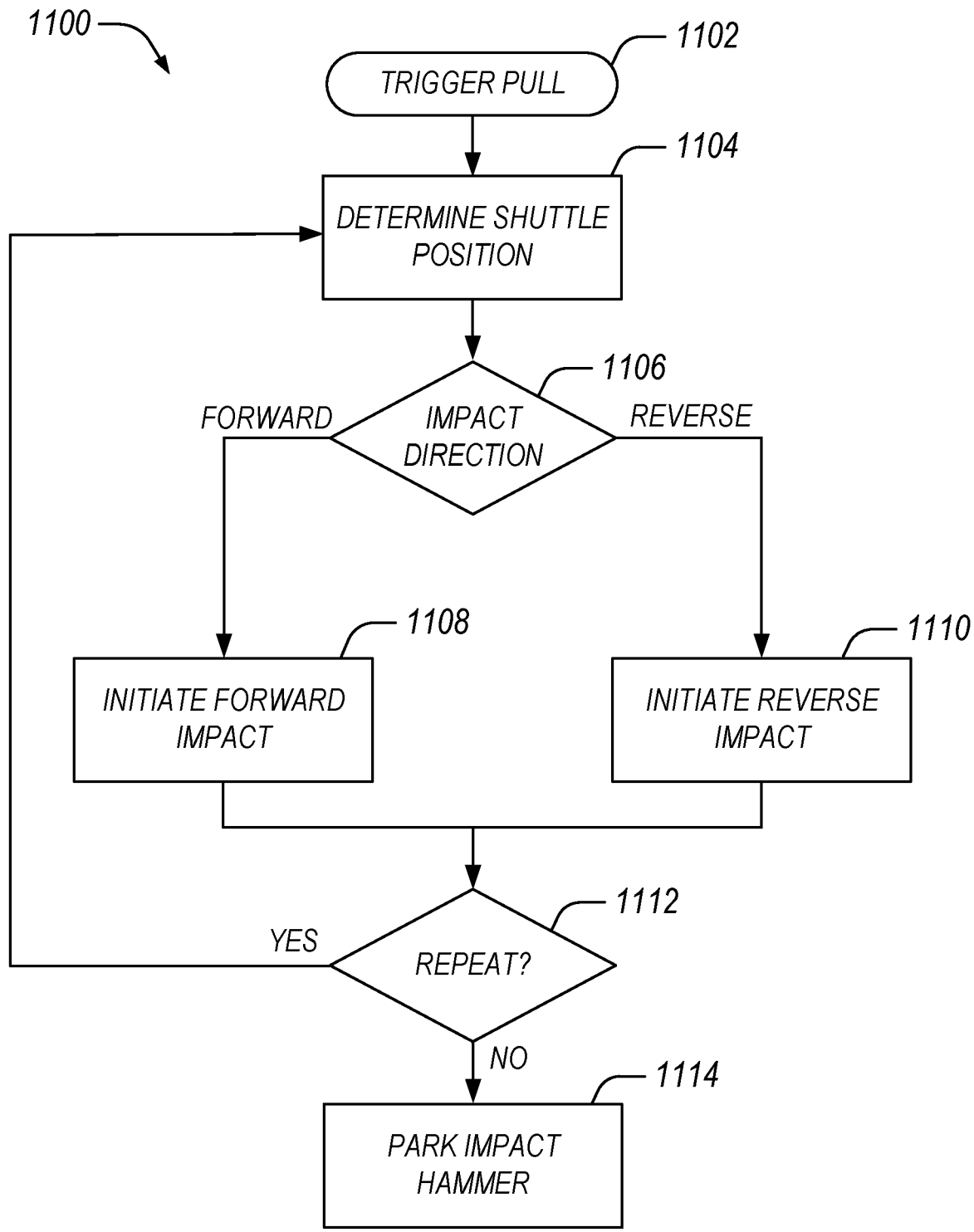
FIG. 11 is a flowchart illustrating a surgeon intent detection technique consistent with at least one example of this disclosure.

FIG. 11 is a flowchart illustrating a surgeon intent detection technique 1100 consistent with at least one example of this disclosure. The surgeon (e.g., user) intent detection technique describes how the impact tool 300 responds to surgeon input to determine which direction to produce impact forces (e.g., forward impacts versus reverse impacts). The technique is implemented within control circuitry that is part of the linear electric motor assembly 320 and more specifically part of the control circuit assembly 322. In this example, the technique 1100 can include operations such as detecting a trigger pull at 1102, determining shuttle housing position at 1104, determining impact direction at 1106, initiating a forward impact at 1108 or initiating a reverse impact at 1110, determining whether to repeat impacts at 1112, and parking the impact hammer at 1114.

In this example, the technique 1100 begins at 1102 with the control circuitry detecting a trigger pull has occurred. At 1104, the technique 1100 continues with the control circuitry interrogating the position sensor assembly 470 to determine shuttle housing 401 position within the impact tool 300. At 1106, the technique 1100 continues with the control circuitry determining an intended impact direction based on the position of the shuttle housing 401. If the position sensor assembly 470 indicates that the shuttle is pushed distally into the impact tool, then a forward impact is intended. If the position sensor assembly 470 indicates that the shuttle is being pulled proximally, then a reverse impact is intended. If the shuttle housing 401 is in a neutral position, the control circuitry will initiate an impact in the same direction as the previous impact.

As part of the operation 1106, the technique 1100 includes the control circuitry receiving position information from both of the position sensors 478. The first option for determining impact intent direction involves a logical flip-flop function. With the logical flip-flop, the output from each of the position sensors is feed through a relay function that includes a pre-defined threshold voltage value resulting in an ON or OFF signal (e.g., binary signal) from each of the position sensors. The binary signals are then feed into a flip-flop circuit, such that if the distal position sensor 478A is ON and the proximal position sensor 478B is off the intent direction is set to forward and if the distal position sensor 478A is OFF and the proximal position sensor 478B is ON the intent direction is set to reverse.

The second option for determining impact intent direction involves merging the outputs of the position sensors and using a relay function to switch between forward intent and reverse intent. In this option, the control circuitry reads the output from each position sensor 478, subtracts an offset from the output values, and feed the result into an arctangent function. The output of the arctangent function is feed through an unwrap function to avoid jumps in the output, with the output of the unwrap function resulting in a linear output of shuttle housing 401 position. The output of the unwrap function is then feed through a relay function with two directional thresholds to switch intent direction. Starting in a distal most position, as the shuttle housing 401 position moves proximally, the forward intent direction is maintained until the processed position data indicates it passes a proximal threshold at which time the intent direction is switched to reverse impacts. The control circuitry maintains the reverse impact intent until the shuttle housing position indicate travel back in a distal direction pass a distal threshold. The proximal and distal thresholds are pre-defined positions that can be programmed within the control circuitry.

At 1108, the technique 1100 continues to initiate a forward impact if the shuttle housing 401 is determined to be positioned more distally within the impact tool 300. In this condition, the control circuitry will trigger a forward impact trajectory that involves moving the hammer assembly 430 distally to a pre-defined position and accelerating the hammer assembly 430 proximally to impact the impact button 412. The control circuitry will determine what intensity setting the tool is on and select a forward impact trajectory accordingly. On a low setting, the hammer assembly 430 can start the forward impact trajectory at a first location that is more proximal than if the tool is set to higher intensity setting. On higher intensity settings, the hammer assembly 430 can be moved close to the distal most range of movement for the linear electric motor assembly 320.

At 1110, the technique 1100 can continue with the control circuitry initiating a reverse impact if the shuttle housing 401 is determined to be positioned more proximally within the impact tool 300. In this condition, the control circuitry will trigger a reverse impact trajectory that involves moving the hammer assembly 430 proximally from a parked position to a pre-defined start position and accelerating the hammer assembly 430 distally to impact the reverse impact cap 416. In an example, the reverse impacts can all be started from the same pre-defined position proximal of a neutral parking position.

At 1112, the technique 1100 continues with the control circuitry determining whether the impact tool 300 is configured for repeated impacts (including whether the trigger remains activated). If no repeated impacts condition is detected, the technique 1100 can conclude at 1114 with the control circuitry commanding the linear electric motor assembly 320 to park the hammer assembly 430. If the repeated impacts condition is detected, then the technique 1100 returns to operation 1104 to determine the shuttle housing 401 position to evaluate surgeon intent for the next impact. The continued monitoring of surgeon intent in this manner allows for impact techniques such as sawing to be performed with the impact tool 300.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A linear electric surgical hammer impact tool comprising:
   a housing defining a cavity extending along a longitudinal axis of the housing;
   a shuttle located inside the cavity and arranged along the longitudinal axis of the housing, the shuttle comprising a first end, a second end, and a wall extending from the first end to the second end, the wall including opposing exterior key grooves extending a length of an exterior portion of the wall;
   a hammer assembly located at least partially within a proximal end of the shuttle and arranged along the longitudinal axis of the housing;
   a linear electric motor configured to drive a piston along the longitudinal axis in a first direction and a second direction; and
   an impact assembly located at least partially within a distal end of the shuttle;
   wherein motion of the hammer assembly in a first direction causes the hammer assembly to contact the first end of the shuttle to generate a forward impact and motion of the hammer assembly in a second direction causes the hammer assembly to contact the second end of the shuttle to generate a reverse impact.

2. The impact tool of claim 1, wherein the hammer assembly includes an impact piston surrounding an impact hammer.

3. The impact tool of claim 2, wherein the impact hammer includes a curved proximal contact surface.

4. The impact tool of claim 3, wherein the curved proximal contact surface includes a radius of 100 mm.

5. The impact tool of claim 2, wherein the impact piston includes a distal circumferential ridge to engage a reverse impact cap to generate reserve impacts.

6. The impact tool of claim 2, wherein the impact assembly includes an impact button adapted to receive impacts from the impact hammer.

7. The impact tool of claim 6, wherein the impact assembly includes an impact interface adapted to transfer impacts received on the impact button to an impact tool held in a chuck adjacent a distal end of the impact tool.

8. The impact tool of claim 6, wherein the impact button is a polymer material and the impact hammer is a dense metal.

9. The impact tool of claim 6, wherein the impact button includes a pocket formed to receive a radiused proximal surface of the impact hammer.

10. The impact tool of claim 1, further comprising a proximal bias spring and a distal bias spring that operate to center the shuttle within the house and absorb excess impact energy.

11. The impact tool of claim 1, further comprising a proximal energy absorption assembly and a distal energy absorption assembly.

12. The impact tool of claim 11, wherein the proximal energy absorption assembly includes a forward absorption ring and a proximal bias ring.

13. The impact tool of claim 12, wherein the forward absorption ring is an energy absorbing rubber and the proximal bias ring is a metallic ring structure adapted to receive a proximal bias spring.

14. The impact tool of claim 1, wherein an impact shaft transmits impact from the impact assembly and extends distally through an impact shaft bearing assembly, the impact shaft bearing assembly operating as a self-aligning shaft bearing on the impact shaft.

15. The impact tool of claim 1, further comprising a position sensor assembly including a slider clip to removably couple a position slider to the shuttle.

16. A method of homing an impact tool, the method comprising:
   operating a linear electric motor to reverse a shuttle mechanism to a distal hard stop;
   monitoring a position sensor assembly during operation of the linear electric motor;
   determining, based on feedback from the position sensor assembly and the linear electric motor, that a distal home position has been reached;
   upon determining that the distal home position was reached, operating the linear electric motor to move the shuttle mechanism to a proximal home position; and
   determining, based on feedback from the position sensor assembly and the linear electric motor, that the proximal home position has been reached.

17. The method of claim 16, wherein the determining the distal home position has been reached includes monitoring voltages on a distal position sensor and a proximal position sensor.

18. The method of claim 16, further comprising calibrating the sensor assembly based on voltage readings at the distal home and proximal home positions.

19. A method of operating an impact tool, the method comprising:
   detecting activation of a trigger mechanism to initiate an impact from the impact tool;
   determining a position of a shuttle assembly within a housing of the impact tool, the shuttle assembly including components adapted to generate an impact;
   determining, from the position of the shuttle assembly, an intended impact direction; and
   delivering an impact in the intended impact direction by operating a linear electric impact mechanism.

20. The method of claim 19, further comprising after delivering the impact, determining, based on a position of the trigger mechanism, whether to repeat delivery of the impact.

21. The method of claim 20, further comprising, upon determining not to repeat delivery of the impact, parking the linear electric impact mechanism.

* * * * *